(12) United States Patent
Agarwal et al.

(10) Patent No.: US 10,107,827 B1
(45) Date of Patent: Oct. 23, 2018

(54) VOLATILE ORGANIC COMPOUND SENSORS, AND METHODS OF MAKING AND USING THE SAME

(71) Applicants: Mangilal Agarwal, Indianapolis, IN (US); Khodadad Varahramyan, Indianapolis, IN (US); Sudhir Shrestha, Indianapolis, IN (US); Ali Daneshkhah, Indianapolis, IN (US)

(72) Inventors: Mangilal Agarwal, Indianapolis, IN (US); Khodadad Varahramyan, Indianapolis, IN (US); Sudhir Shrestha, Indianapolis, IN (US); Ali Daneshkhah, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 472 days.

(21) Appl. No.: 14/685,231

(22) Filed: Apr. 13, 2015

Related U.S. Application Data

(60) Provisional application No. 61/978,490, filed on Apr. 11, 2014, provisional application No. 61/978,567, filed on Apr. 11, 2014.

(51) Int. Cl.
| | |
|---|---|
| *G01N 33/497* | (2006.01) |
| *G01N 33/98* | (2006.01) |
| *G01N 33/64* | (2006.01) |
| *G01N 33/18* | (2006.01) |
| *G01N 33/50* | (2006.01) |
| *C08L 79/04* | (2006.01) |
| *C08L 33/12* | (2006.01) |

(52) U.S. Cl.
CPC .............. *G01N 33/98* (2013.01); *C08L 33/12* (2013.01); *C08L 79/04* (2013.01); *G01N 33/18* (2013.01); *G01N 33/50* (2013.01); *G01N 33/64* (2013.01)

(58) Field of Classification Search
CPC ........ G01N 33/18; G01N 33/50; G01N 33/64; G01N 33/98; C08L 33/12; C08L 79/04
See application file for complete search history.

(56) References Cited

U.S. PATENT DOCUMENTS

2009/0272946 A1* 11/2009 Lu ........................... H01B 1/04
                                                         252/511
2012/0055257 A1* 3/2012 Shaw-Klein .......... H01L 41/081
                                                         73/780

* cited by examiner

*Primary Examiner* — Robert Eom
(74) *Attorney, Agent, or Firm* — Quarles & Brady LLP

(57) ABSTRACT

A biomedical sensor and sensor system for analysis of breath are disclosed. The biomedical sensor can include two layers arranged to swell or contract in a plane perpendicular to an axial direction while being restricted from swelling in the axial direction. The biomedical sensor includes resistance connections to allow measurement of the resistance of each layer and a combined resistance of both layers. The sensor system can include one, two, or three or more sensors, each having a pair of electrodes separated by a gap and one or more layers of composite material located within the gap. the sensor system includes resistance circuits configured to measure changes in resistance between the electrodes. A polypyrrole/polymethyl methacrylate/polyethylene glycol composite material and method of making the same are disclosed.

7 Claims, 23 Drawing Sheets
(23 of 23 Drawing Sheet(s) Filed in Color)

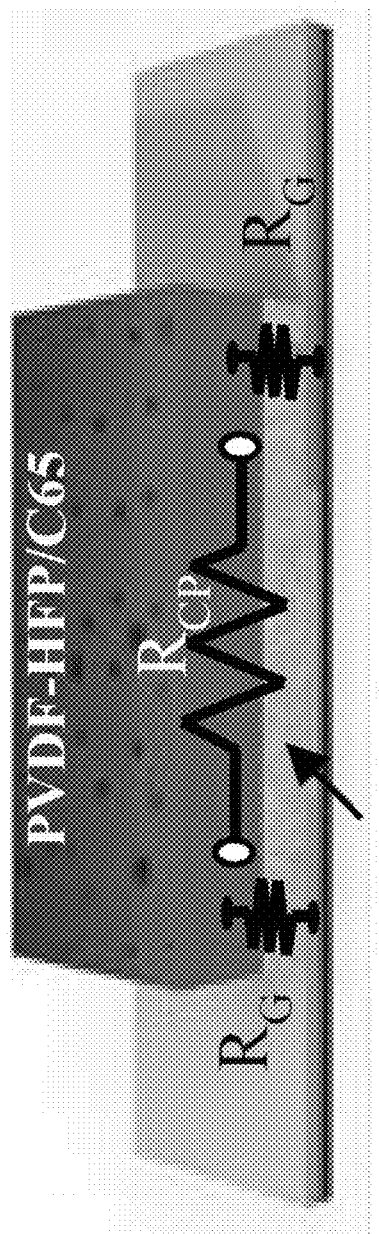
FIG. 21(a)
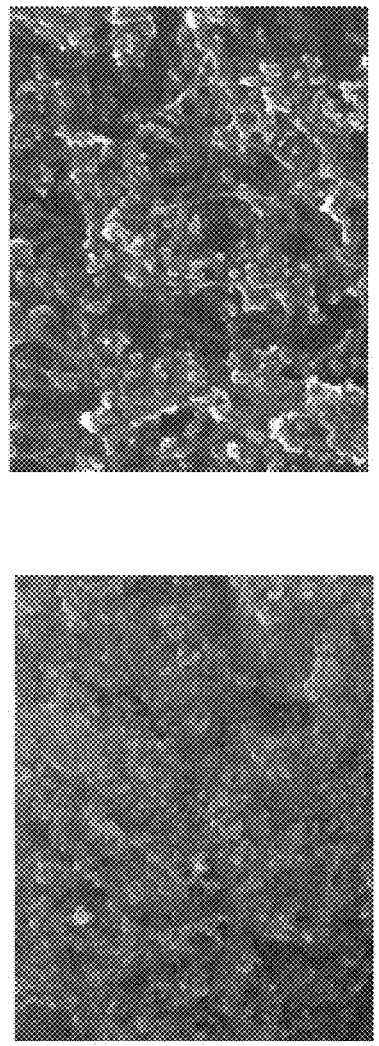
FIG. 21(c)
FIG. 21(b)

VOLATILE ORGANIC COMPOUND SENSORS, AND METHODS OF MAKING AND USING THE SAME

CROSS-REFERENCE TO RELATED APPLICATIONS

This application claims priority to U.S. Provisional Patent Application No. 61/978,490, filed Apr. 11, 2014, the entire contents of which are incorporated herein in their entirety by reference. This application is related to U.S. patent application Ser. No. 14/685,298, filed Apr. 13, 2015, and U.S. Provisional Patent Application No. 61/978,567, filed Apr. 11, 2014, the entire contents of which are incorporated herein in their entirety by reference.

STATEMENT REGARDING FEDERALLY SPONSORED RESEARCH

N/A

BACKGROUND

The disclosure relates generally to composite materials and sensors. More particularly, the disclosure relates to methods and systems directed to sensing the presence of one or more analytes of interest (e.g., volatile organic compounds) in a target fluid (e.g., the human breath).

Timely detection of health conditions can provide potentially life-saving information to patients. Human breath has been shown to contain VOC biomarkers that can be used to identify numerous diseases. These VOCs allow for many applications of noninvasive detection of diseases and other biological metrics. Acetone levels in breath are a significant indicator of the presence of diabetes, a disease that threatens the lives of millions of people in the US and around the world. Moreover, links have been reported between breath isoprene level and oxidative stress, blood cholesterol level, and increased breath and heart rate. Ethanol has been shown to have potential medical applications for diabetes detection. Esters similar to 2-ethylhexyl acetate are common in breath and have been linked to multiple diseases, including lung cancer. These and other VOCs can be used to non-invasively detect and monitor human health conditions. For example, diabetes patients experience rapid changes in their blood glucose levels throughout the day and may experience potentially life threatening conditions. However, reliable non-invasive methods for monitoring blood glucose levels currently do not exist. A sensor array that can monitor symptoms of diabetes by analyzing breath VOCs, most importantly: acetone, can offer lifesaving information for such patients.

Diabetes threatens the lives of millions of people in the US and around the world. Diabetes patients experience rapid changes in their blood glucose levels throughout the day and may experience potentially life threatening conditions. The finger prick glucometer is the most commonly employed method for glucose measurement, however, continuous glucose monitors (CGMs) have also been recently used when needed. As these and other currently utilized blood glucose measurement techniques are invasive, a non-invasive method for accurately detecting elevated blood glucose levels could provide lifesaving information to diabetic patients. Blood glucose level variation can manifest itself in many different ways in the human body. The design and fabrication of a noninvasive glucose sensor which estimates blood glucose sugar based on the analysis of volatile organic compounds (VOCs) including acetone in exhaled breath can offer lifesaving information for such patients. The interaction of red blood cells with alveolar air in the lungs leaves a foot print of the VOCs from blood in the exhaled breath. An increase in blood glucose levels changes the metabolic behavior of the body and changes the VOC footprint. Recent studies have resulted in more evidence for the existence of a linkage between exhaled acetone and blood glucose levels in diabetes patients. The findings have been supported by the fact that due to lack of insulin, ketoacidosis increases the plasma acetone concentration.

Two of the major challenges in developing breath VOC sensors are as follows: (1) a need to be highly sensitive because the concentrations of VOC biomarkers in exhaled breath are extremely low and (2) a need to be highly selective in detecting the target VOCs due to the presence of hundreds of gaseous components in breath, including water vapor. The human sense of smell works well in the presence of water as the olfactory receptors are not sensitive to water. However, sensors developed to detect VOCs often exhibit a high response to water, which interferes with the detection of the target agents. This has been a major challenge in developing electronic noses for breath VOC detection applications. These requirements have encouraged researchers to consider a wide range of materials including: CNT, graphene, carbon black, gold nanoparticles, metal oxides, and various polymers. Gold nanoparticle-based sensors have also shown promise in the detection of low-concentration breath VOCs. However, high sensitivity to water is problematic with these sensors. Conducting polymers have been shown to detect acetone at room temperature, yet these sensors often suffer from high sensitivity to moisture and performance degradation over time. Carbon-based materials, including CNT, carbon black, and graphene have also been investigated intensely for breath VOC sensing applications. Pristine CNTs do not efficiently adsorb VOCs, but functionalization improves their performance for sensor applications. Functionalization of CNTs with carboxylic groups and defect sites on CNTs created through acid sonication have shown improved adsorption of organic compounds and detection of low concentration VOCs. Interestingly, these processes also increase the response to water. Polymer-coated CNTs and polymer carbon black composites have also been utilized in detecting breath VOCs. CNT, carbon black and polymer composites have been used to achieve high sensitivity and response time. In CNT polymer composites, the swelling or contraction of polymers changes the separation between the conducting CNT material, which alters the resistance. These CNT polymer composite-based sensors have been shown to have both high sensitivity and selectivity. However, these sensors suffer from poor selectivity due to their high response to water molecules. For example, CNT/poly(ethyleneterephthalate) (PET) sensor has been reported to exhibit a 2.7 times higher responsiveness to water than to acetone. Carbon black (C65) composites with low-density polyethylene (LDPE) and poly(ethylene-block-ethylene oxide) (PE-b-PEO), polyethylene glycol (PEG), and poly methyl methacrylate (PMMA) have been used to detect acetone, however, their acetone selectivity in the presence water is still poor. Adsorption of water molecules have also been known to accelerate sensor degradation. Composites of PVDF-HFP, previously reported in battery and piezoelectric device applications, exhibit better material stability and more hydrophobic properties compared to PVDF, PMMA, or PEG. PVDF-HFP is also known to swell when exposed to acetone. However, PVDF-HFP itself is a poor electrical conductor, therefore requires infusion of conducting particles to form chemiresistive sensors.

Metal oxides have offered promising features for detecting very low concentrations of acetone. Generally, high sensitivity metal oxide based sensors are operated at an elevated temperature, resulting in higher energy consumption. Conducting composite polymers present another method for detecting acetone. The swelling effect of PMMA by acetone has been widely studied. The conductivity of PMMA can be improved by adding PPy to form a resistive based acetone sensor. A film composed of carbon nanotubes with PMMA has been reported to detect low concentrations of acetone. However, these sensors are also known to suffer from poor selectivity.

Consequently, considering such limitations of previous technological approaches, it would be desirable to have a system and method for a highly sensitive acetone sensor applicable in non-invasive detection of blood glucose level from human breath.

SUMMARY

The present disclosure overcomes the aforementioned drawbacks by presenting a PPy/PMMA/PEG composite material, methods of making the PPy/PMMA/PEG composite material, a pellet based sensor consisting of two PPy/PMMA/PEG and PPy/PMMA surfaces that together provide a higher selectivity, and methods of using the sensor. In the sensor of the present disclosure, the changes in the resistances on the two surfaces and across the two layers are measured separately. As the PPy/PMMA/PEG and PPy/PMMA responds differently to various gasses, collectively they provide the higher selectivity needed to detect acetone in human breath.

In one aspect, the present disclosure provides a PPy/PMMA/PEG composite material consists essentially of: PPy; PMMA; and PEG.

In another aspect, the present disclosure provides a method of preparing a PPy/PMMA/PEG composite material includes: performing chemical oxidative polymerization of pyrrole in the presence of polymethyl methacrylate (PMMA) to produce a post-oxidative polymerization solution comprising a PPy/PMMA composite; isolating the PPy/PMMA composite from the post-oxidative polymerization solution; dissolving the PPy/PMMA composite in chloroform to form a PPy/PMMA chloroform solution; contacting the PPy/PMMA chloroform solution with PEG to form a PPy/PMMA/PEG chloroform solution; sonicating the PPy/PMMA/PEG solution; and drying the PPy/PMMA/PEG solution to form the PPy/PMMA/PEG composite material.

In yet another aspect, the present disclosure provides a biomedical sensor for analysis of breath includes a combined sensing layer oriented perpendicular to an axial direction, the combined sensing layer comprising: a first layer oriented perpendicular to the axial direction, the first layer consisting essentially of a first composite material; a second layer disposed adjacent to the first layer in the axial direction and in contact with the first layer, the second layer consisting essentially of a second composite material; and a plurality of resistance connections sufficient to enable measurement of one or more of a first resistance of the first layer, a second resistance of the second layer, and a third resistance of the combined sensing layer, wherein the first layer and second layer are configured to swell or contract in a plane perpendicular to the axial direction, and wherein the combined sensing layer is restricted from swelling in the axial direction.

In a further aspects, the present disclosure provides a biomedical sensor system for analysis of breath. The sensor system can include a first sensor, a second sensor, or a third sensor. The first sensor can include two first sensor electrodes separated by a first sensor gap; a first sensor composite material located in the first sensor gap and contacting the two first sensor electrodes, the first sensor composite material consisting essentially of a first poly(vinylidene fluoride-hexafluoropropylene) (PVDF-HFP) composite having a plurality of carbon black particles embedded therein; and a first sensor resistance measurement circuit coupled to the two first sensor electrodes and configured to measure a change in resistance between the two first sensor electrodes. The second sensor can include two second sensor electrodes separated by a second sensor gap; a second sensor polymeric material located in the second sensor gap and covering the at least part of the two second sensor electrodes; a second sensor composite material contacting the second sensor polymeric material, the second sensor composite material consisting essentially of a second PVDF-HFP composite having a plurality of carbon black particles embedded therein; and a second sensor resistance measurement circuit coupled to the two second sensor electrodes and configured to measure a change in resistance between the two second sensor electrodes. The third sensor can include two third sensor electrodes separated by a third sensor gap; a third sensor composite material located in the third sensor gap and contacting the two third sensor electrodes, the third sensor composite material consisting essentially of a third PVDF-HFP composite having a plurality of carbon black particles and a plurality of carbon nanotubes embedded therein; and a third sensor resistance measurement circuit coupled to the third sensor electrodes and configured to measure a change in resistance between the two third sensor electrodes.

The foregoing and other aspects and advantages of the disclosure will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 21(a) is a schematic representation of Sensor-2 of Example 6.

FIG. 21(b) is an SEM image of a spin-coated PVDF-HFP/C65 composite, as described in Example 6.

FIG. 21(c) is an SEM image of a spin-coated PVDF-HFP/C65/CNT composite, as described in Example 7.

DETAILED DESCRIPTION

Figure 1:
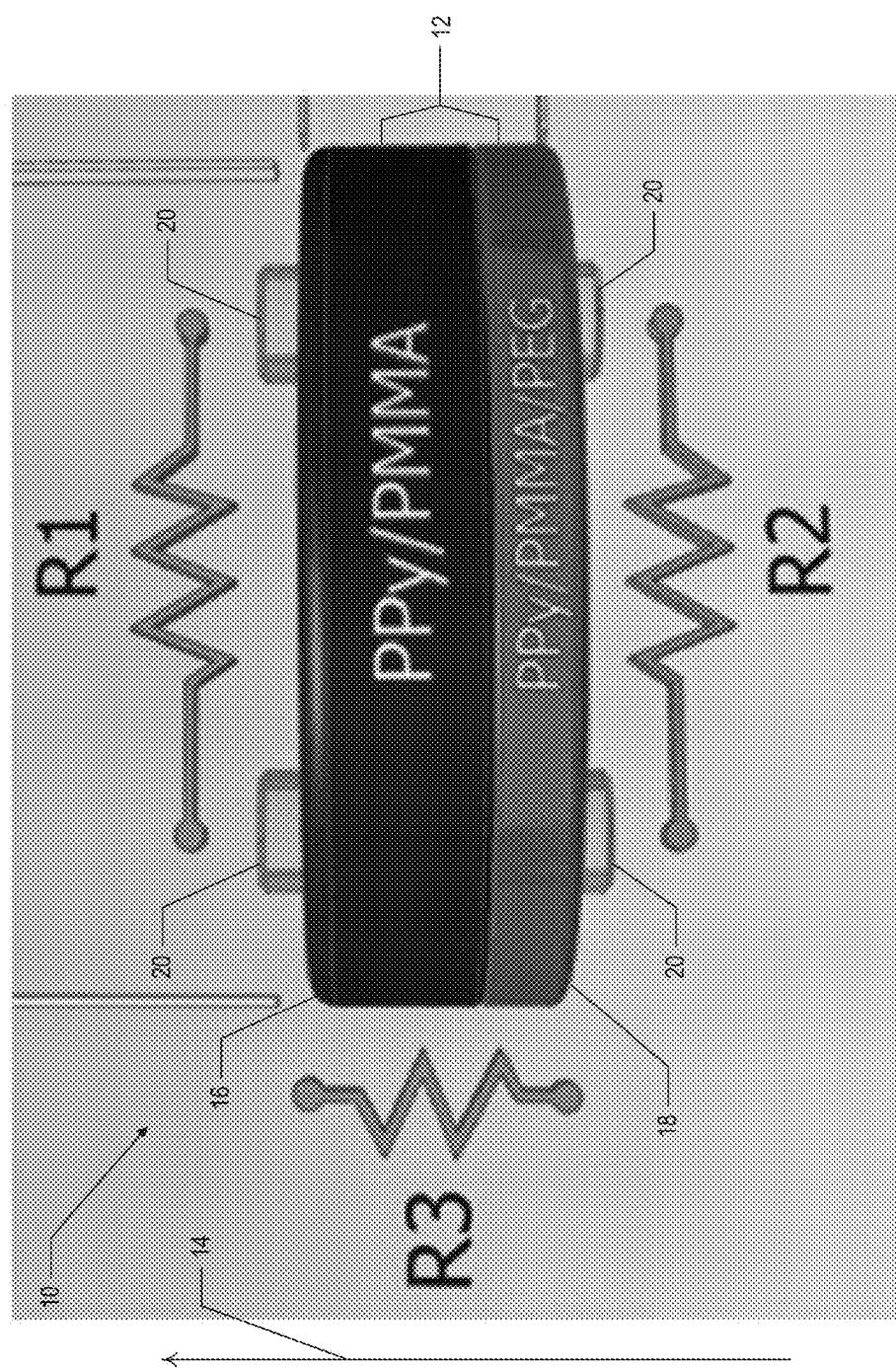
FIG. 1 is a schematic of a sensor according to one aspect the present disclosure.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise. Where a range of values is recited, this disclosure contemplates all combinations of the upper and lower bounds of those ranges that are not explicitly disclosed. For example, if ranges of 1 to 10 and 2 to 9 are disclosed, this disclosure contemplates ranges of 1 to 9 and 2 to 10.

Specific structures, devices, compositions, and methods relating to detection of volatile organic compounds are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

This disclosure provides a PPy/PMMA/PEG composite material, a method of making a PPy/PMMA/PEG composite material, and a sensor comprising two PPy/PMMA/PEG and PPy/PMMA surfaces that together provide a higher selectivity. In the proposed sensor, the changes in the resistances on the two surfaces and across the two layers are measured separately. As the PPy/PMMA/PEG and PPy/PMMA responds differently to various gasses, collectively they provide the higher selectivity needed to detect acetone in human breath. The material fabrication and characterization, sensor fabrication and testing, and experimental results are presented and discussed.

As used herein, the term "composite material" shall refer to material that contains two or more different materials where the different materials remain physically or chemically distinct from one another after being combined.

As used herein, the term "resistance connection" shall refer to any means of measuring the resistance of a material, for example an electrical lead or an exposed area suitable for contact by a resistance probe.

I. PPy/PMMA/PEG Composite Materials

This disclosure provides a PPy/PMMA/PEG composite material consisting essentially of: PPy; PMMA; and PEG.

The PPy may be present in the PPy/PMMA/PEG composite material in an amount ranging from about 1% by weight to about 99% by weight of the composite material, or an amount ranging from about 10% by weight to about 90% by weight of the composite material. In certain aspects, the PPy may be present in the PPy/PMMA/PEG composite material in an amount of at least about 10% by weight of the composite material, at least about 15%, at least about 20%, at least about 25%, at least about 30%, at least about 35%, at least about 40%, at least about 45%, or at least about 50% by weight of the composite material. In certain aspects, the PPy may be present in the PPy/PMMA/PEG composite material in an amount of at most about 90% by weight of the composite material, at most about 85%, at most about 80%, at most about 75%, at most about 70%, at most about 65%, at most about 60%, at most about 55%, or at most about 50% by weight of the composite material.

The PPy may have a molecular weight ranging from about 67.09 g/mol to about 33,545 g/mol. In certain aspects, the PPy may have a molecular weight of at least about 67.09 g/mol, at least about 100 g/mol, at least about 200 g/mol, at least about 500 g/mol, at least about 1000 g/mol, at least about 2000 g/mol, at least about 5000 g/mol, or at least about 10,000 g/mol. In certain aspects, the PPy may have a molecular weight of at most about 33,545 g/mol, at most about 25,000 g/mol, at most about 20,000 g/mol, at most about 15,000 g/mol, at most about 10,000 g/mol, at most about 5000 g/mol, at most about 2500 g/mol, or at most about 1000 g/mol.

The PMMA may be present in the PPy/PMMA/PEG composite material in an amount ranging from about 0.001% by weight to about 99% by weight of the composite material. In certain aspects, the PMMA may be present in the PPy/PMMA/PEG composite material in an amount of at least about 0.001% by weight of the composite material, at least about 1%, at least about 2%, at least about 5%, at least about 10%, at least about 15%, at least about 20%, at least about 25%, at least about 30%, at least about 35%, at least about 40%, at least about 45%, or at least about 50% by weight of the composite material. In certain aspects, the PMMA may be present in the PPy/PMMA/PEG composite material in an amount of at most about 99% by weight of the composite material, at most about 95%, at most about 90%, at most about 85%, at most about 80%, at most about 75%, at most about 70%, at most about 65%, at most about 60%, at most about 55%, or at most about 50% by weight of the composite material.

The PMMA may have a molecular weight ranging from about 1900 g/mol to about 996,000 g/mol. In certain aspects, the PMMA may have a molecular weight of at least about 1900 g/mol, at least about 2500 g/mol, at least about 5000 g/mol, at least about 10,000 g/mol, at least about 25,000 g/mol, at least about 50,000 g/mol, at least about 100,000 g/mol, at least about 250,000 g/mol, or at least about 500,000 g/mol. In certain aspects, the PMMA may have a molecular weight of at most about 996,000 g/mol, at most about 900,000 g/mol, at most about 750,000 g/mol, at most about 500,000 g/mol, at most about 400,000 g/mol, at most about 300,000 g/mol, at most about 200,000 g/mol, at most about 100,000 g/mol, at most about 75,000 g/mol, at most about 50,000 g/mol, or at most about 10,000 g/mol.

The PEG may be present in the PPy/PMMA/PEG composite material in an amount ranging from about 0.001% by weight to about 99% by weight of the composite material. In certain aspects, the PEG may be present in the PPy/PMMA/PEG composite material in an amount of at least about 0.001% by weight of the composite material, at least about 1%, at least about 2%, at least about 5%, at least about 10%, at least about 15%, at least about 20%, at least about 25%, at least about 30%, at least about 35%, at least about 40%, at least about 45%, or at least about 50% by weight of the composite material. In certain aspects, the PEG may be present in the PPy/PMMA/PEG composite material in an amount of at most about 99% by weight of the composite material, at most about 95%, at most about 90%, at most about 85%, at most about 80%, at most about 75%, at most about 70%, at most about 65%, at most about 60%, at most about 55%, or at most about 50% by weight of the composite material.

The PEG may have a molecular weight ranging from about 100,000 g/mol to about 8,000,000 g/mol. In certain aspects, the PEG may have a molecular weight of at least about 100,000 g/mol, at least about 200,000 g/mol, at least about 300,000 g/mol, at least about 400,000 g/mol, at least about 500,000 g/mol, at least about 750,000 g/mol, at least about 1,000,000 g/mol, at least about 2,000,000 g/mol, at least about 3,000,000 g/mol, at least about 4,000,000 g/mol, or at least about 5,000,000 g/mol. In certain aspects, the PEG may have a molecular weight of at most about 8,000,000 g/mol, at most about 7,500,000 g/mol, at most about 6,000,000 g/mol, at most about 5,000,000 g/mol, at most about 4,000,000 g/mol, at most about 3,000,000 g/mol, at most about 2,000,000 g/mol, or at most about 1,000,000 g/mol.

As used herein, molecular weight can refer to a number average molecular weight, a mass average molecular weight, a viscosity average molecular weight, an average molar mass, or other molecular weight representations known to a person having ordinary skill in the art.

In certain aspects, the PPy/PMMA/PEG composite material may have a mechanical or electrical property that is improved by at least about 0.001%, at least about 0.1%, at least about 1%, at least about 5%, at least about 10%, at least about 25%, or at least about 50% relative to a composite material having 0% PEG but otherwise has a proportion of constituents that is identical to the PPy/PMMA/PEG composite material. In certain applications, the mechanical property is flexibility. In certain applications, the electrical property is conductivity.

The PPy/PMMA/PEG composite material may exhibit a change in an electrical property upon exposure to an analyte of interest. In certain aspects, the analyte of interest is a volatile organic compound, such as acetone, ethanol, water, isoprene, $NO_2$, $NH_3$, acetate acid, $CO_2$, ethane, pentane, 2-propanol, alkanes and the like. In certain applications, the analyte of interest is acetone.

The PPy/PMMA/PEG composite material may exhibit a change in an electrical property upon exposure to an analyte of interest in an amount of less than about 1 part per thousand. In certain applications, the PPy/PMMA/PEG composite material may exhibit a change in an electrical property upon exposure to an analyte of interest in an amount of less than about 300 ppm.

II. Methods of Preparing a PPy/PMMA/PEG Composite Material

This disclosure also provides a method of preparing a PPy/PMMA/PEG composite material. In certain aspects, the method may comprise one or more of the following steps: performing chemical oxidative polymerization of pyrrole in the presence of polymethyl methacrylate (PMMA) to produce a post-oxidative polymerization solution comprising a PPy/PMMA composite; isolating the PPy/PMMA composite from the post-oxidative polymerization solution; dissolving the PPy/PMMA composite in chloroform to form a PPy/PMMA chloroform solution; contacting the PPy/PMMA chloroform solution with PEG to form a PPy/PMMA/PEG chloroform solution; sonicating the PPy/PMMA/PEG solution; and drying the PPy/PMMA/PEG solution to form the PPy/PMMA/PEG composite material.

The PPy, PMMA, and PEG of the method may have the same properties as set forth herein with respect to the PPy/PMMA/PEG composite material.

In general, chemical oxidative polymerization techniques that are capable of producing PPy with the material properties described herein are suitable for use with the present disclosure. In certain aspects, performing chemical oxidative polymerization of pyrrole in the presence of PMMA may further comprise the presence of a surfactant (e.g., polystyrene sulfonate (PSS)) or an oxidant (e.g., ammonium persulfate (APS)) in addition to PMMA. In certain aspects, performing chemical oxidative polymerization of pyrrole in the presence of PMMA may be performed in a solvent selected from the group consisting of water, chloroform, toluene, ethanol, and acetone, and combinations thereof.

The chemical oxidative polymerization may be performed in the presence of an amount of surfactant ranging from about 1% w/w to about 50% w/w. Surfactants suitable for use in the present disclosure include, but are not limited to, PSS, NADBS, PEG, various derivatives of arylsulfonates, chloride, anionic spherical polyelectrolyte brushes, Dodecylbenzenesulphonic acid and combinations thereof.

The chemical oxidative polymerization may be performed in the presence of an amount of oxidant ranging from about 0.1 g to about 10 g for 200 ml solvent. Oxidants suitable for use in the present disclosure include, but are not limited to, APS, ferric chloride ($FeCl_3$), cetrimonium persulfate (CTA) 2S2O8, and combinations thereof.

The chemical oxidative polymerization may be performed at a temperature ranging from about 0° C. to about 80° C. In certain aspects, the chemical oxidative polymerization may be performed at a temperature of at least about 0° C., at least about 1° C., at least about 2° C., at least about 3° C., at least about 4° C., at least about 5° C., at least about 10° C., at least about 15° C., at least about 20° C., at least about 25° C., at least about 30° C., at least about 35° C., at least about 40° C., at least about 45° C., at least about 50° C. In certain aspects, the chemical oxidative polymerization may be performed at a temperature of at most about 80° C., at most about 75° C., at most about 70° C., at most about 65° C., at most about 60° C., at most about 55° C., at most about 50° C., at most about 45° C., at most about 40° C., at most about 35° C., at most about 30° C., at most about 25° C., at most about 20° C., at most about 15° C., at most about 10° C., or at most about 5° C.

The chemical oxidative polymerization may be performed for a length of time ranging from about 1 minute to about 72 hours. In certain aspects, the chemical oxidative polymerization may be performed for a length of time of at least about 1 minute, at least about 5 minutes, at least about 10 minutes, at least about 15 minutes, at least about 30 minutes, at least about 45 minutes, at least about 1 hour, at least about 2 hours, at least about 3 hours, at least about 4 hours, at least about 5 hours, at least about 6 hours, at least about 9 hours, at least about 12 hours, at least about 15 hours, at least about 18 hours, at least about 21 hours, at least about 24 hours, at least about 36 hours, at least about 48 hours, or at least about 60 hours. In certain aspects, the chemical oxidative polymerization may be performed for a length of time of at most about 72 hours, at most about 66 hours, at most about 60 hours, at most about 54 hours, at most about 48 hours, at most about 42 hours, at most about 36 hours, at most about 30 hours, at most about 24 hours, at most about 22 hours, at most about 20 hours, at most about 18 hours, at most about 16 hours, at most about 14 hours, at most about 12 hours, at most about 10 hours, at most about 8 hours, at most about 6 hours, at most about 4 hours, at most about 2 hours, at most about 1 hour, at most about 45 minutes, or at most about 30 minutes.

Isolating may comprise filtering or other similar means of isolating a material. In certain aspects, isolating the PPy/PMMA composite from the post-oxidative polymerization solution may comprise filtering the post-oxidative solution to collect the PPy/PMMA composite.

In certain aspects, the methods may further comprise drying the PPy/PMMA composite. Drying the PPy/PMMA composite may further comprise exposing the PPy/PMMA composite to a vacuum.

Drying the PPy/PMMA composite may be conducted at temperatures ranging from about 10° C. to about 100° C. and for a length of time ranging from about 10 minutes to about 72 hours. In certain aspects, drying the PPy/PMMA composite may be conducted at a temperature of at least about 10° C., at least about 20° C., at least about 30° C., at least about 40° C., at least about 50° C., at least about 60° C., at least about 70° C., at least about 80° C., or at least about 90° C. In certain aspects, drying the PPy/PMMA composite may be conducted at a temperature of at most about 100° C., at most about 90° C., at most about 80° C., at most about 70° C., at most about 60° C., at most about 50° C., at most about 40° C., at most about 30° C., or at most about 20° C. In certain aspects, drying the PPy/PMMA composite may be conducted for a length of time of at least about 10 minutes, at least about 15 minutes, at least about 30 minutes, at least about 45 minutes, at least about 1 hour, at least about 2 hours, at least about 3 hours, at least about 4 hours, at least about 5 hours, at least about 6 hours, at least about 9 hours, at least about 12 hours, at least about 15 hours, at least about 18 hours, at least about 21 hours, at least about 24 hours, at least about 36 hours, at least about 48 hours, or at least about 60 hours. In certain aspects, drying the PPy/PMMA composite may be performed for a length of time of at most about 72 hours, at most about 66 hours, at most about 60 hours, at most about 54 hours, at most about 48 hours, at most about 42 hours, at most about 36 hours, at most about 30 hours, at most about 24 hours, at most about 22 hours, at most about 20 hours, at most about 18 hours, at most about 16 hours, at most about 14 hours, at most about 12 hours, at most about 10 hours, at most about 8 hours, at most about 6 hours, at most about 4 hours, at most about 2 hours, at most about 1 hour, at most about 45 minutes, or at most about 30 minutes.

Dissolving the PPy/PMMA composite in chloroform solution to form a PPy/PMMA chloroform solution may comprise dissolving PPy/PMMA in an amount suitable to produce a concentration ranging from about 0.0001 g/ml to about 0.1 g/ml in an amount of chloroform ranging from about 1 ml to about 100 ml. In certain aspects, dissolving the PPy/PMMA composite in chloroform solution to form a PPy/PMMA chloroform solution may comprise dissolving PPy/PMMA in an amount suitable to produce a concentration of at least about 0.0001 g/ml, at least about 0.0005 g/ml, at least about 0.001 g/ml, at least about 0.005 g/ml, at least about 0.01 g/ml, at least about 0.05 g/ml. In certain aspects, dissolving the PPy/PMMA composite in chloroform solution to form a PPy/PMMA chloroform solution may comprise dissolving PPy/PMMA in an amount suitable to produce a concentration of at most about 0.1 g/ml, at most about 0.05 g/ml, at most about 0.01 g/ml, at most about 0.005 g/ml, at most about 0.001 g/ml, or at most about 0.0005 g/ml. In certain aspects, dissolving the PPy/PMMA composite in chloroform solution to form a PPy/PMMA chloroform solution may comprise dissolving PPy/PMMA in an amount of chloroform of at least about 1 ml, at least about 5 ml, at least about 10 ml, at least about 25 ml, or at least about 50 ml. In certain aspects, dissolving the PPy/PMMA composite in chloroform solution to form a PPy/PMMA chloroform solution may comprise dissolving PPy/PMMA in an amount of chloroform of at most about 100 ml, at most about 75 ml, at most about 50 ml, at most about 25 ml, or at most about 10 ml.

Contacting the PPy/PMMA chloroform solution with PEG may comprise a means of contacting known to those skilled in the art. For example, contacting the PPy/PMMA chloroform solution with PEG may comprise stirring, mixing, adding, and the like.

Sonicating the PPy/PMMA/PEG solution may comprise bath sonicating, rod sonicating, stirring, mixing, and combinations thereof. In certain aspects, sonicating the PPy/PMMA/PEG solution may comprise sonicating at a frequency ranging from about 20 kHz to about 55 kHz. In certain aspects, sonicating the PPy/PMMA/PEG solution may comprise sonicating at a frequency of at least about 20 kHz, at least about 25 kHz, at least about 30 kHz, at least about 35 kHz, at least about 40 kHz, at least about 45 kHz, or at least about 50 kHz. In certain aspects, sonicating the PPy/PMMA/PEG solution may comprise sonicating at a frequency of at most about 55 kHz, at most about 50 kHz, at most about 45 kHz, at most about 40 kHz, at most about 35 kHz, at most about 30 kHz, or at most about 25 kHz.

In certain aspects, sonicating the PPy/PMMA/PEG solution may be performed for a length of time ranging from about 1 minute to about 72 hours. In certain aspects, sonicating the PPy/PMMA/PEG solution may be performed for a length of time of at least about 1 minute, at least about 5 minutes, at least about 10 minutes, at least about 15 minutes, at least about 30 minutes, at least about 45 minutes, at least about 1 hour, at least about 2 hours, at least about 3 hours, at least about 4 hours, at least about 5 hours, at least about 6 hours, at least about 9 hours, at least about 12 hours, at least about 15 hours, at least about 18 hours, at least about 21 hours, at least about 24 hours, at least about 36 hours, at least about 48 hours, or at least about 60 hours. In certain aspects, sonicating the PPy/PMMA/PEG solution may be performed for a length of time of at most about 72 hours, at most about 66 hours, at most about 60 hours, at most about 54 hours, at most about 48 hours, at most about 42 hours, at most about 36 hours, at most about 30 hours, at most about 24 hours, at most about 22 hours, at most about 20 hours, at most about 18 hours, at most about 16 hours, at most about 14 hours, at most about 12 hours, at most about 10 hours, at most about 8 hours, at most about 6 hours, at most about 4 hours, at most about 2 hours, at most about 1 hour, at most about 45 minutes, or at most about 30 minutes. In certain aspects, sonicating the PPy/PMMA/PEG solution may be performed at a temperature ranging from about 0° C. to about 50° C. In certain aspects, sonicating the PPy/PMMA/PEG solution may be performed at a temperature of at least about 0° C., at least about 10° C., at least about 20° C., at least about 30° C., or at least about 40° C. In certain aspects, sonicating the PPy/PMMA/PEG solution may be performed at a temperature of at most about 50° C., at most about 40° C., at most about 30° C., at most about 20° C., or at most about 10° C.

Drying the PPy/PMMA/PEG solution to form the PPy/PMMA/PEG composite material may comprise means of drying a solution known to those skilled in the art, for example, exposing the PPy/PMMA/PEG solution to a vacuum. In certain aspects, drying the PPy/PMMA/PEG solution to form the PPy/PMMA/PEG composite material may be conducted at temperatures ranging from about 0° C. to about 100° C., and for a length of time ranging from about 10 minutes to about 72 hours. In certain aspects, drying the PPy/PMMA/PEG solution to form the PPy/PMMA/PEG composite material may be conducted a temperatures and for a length of time of at least and at most those set forth above with respect to drying the PPy/PMMA composite.

III. Sensors

This disclosure further provides sensors. In certain aspects, the sensors may be biomedical. In certain aspects, the sensors may be used for the analysis of breath, in particular, human breath. In certain aspects, the sensors may be smart sensors.

Referring to FIG. 1, the sensor 10 may comprise a combined sensing layer 12. The combined sensing layer 12 can be oriented perpendicular to an axial direction 14. In certain aspects, the combined sensing layer 12 can comprise a PPy/PMMA/PEG composite material layer and a PPy/PMMA composite material layer.

The combined sensing layer 12 may have a thickness in the axial direction 14 ranging from about 3 μm to about 1 cm. In certain aspects, the combined sensing layer 12 may have a thickness in the axial direction 14 of at least about 3 μm, at least about 10 μm, at least about 100 μm, at least about 1 mm, at least about 10 mm, or at least about 100 mm. In certain aspects, the combined sensing layer 12 may have a thickness in the axial direction 14 of at most about 1 cm, at most about 100 mm, at most about 10 mm, at most about 1 mm, at most about 100 μm, at most about 50 μm, or at most about 10 μm.

The combined sensing layer 12 may have a physical dimension perpendicular the axial direction 14 ranging from about 10 micrometer diameter to about to 1 centimeter diameter. In certain aspects, the combined sensing layer 12 may have a physical dimension perpendicular to the axial direction 14 of at least about 10 μm, at least about 100 μm, at least about 1 mm, at least about 10 mm, or at least about 100 mm. In certain aspects, the combined sensing layer 12 may have a physical dimension perpendicular to the axial direction 14 of at most about 1 cm, at most about 100 mm, at most about 10 mm, at most about 1 mm, or at most about 100 μm.

The combined sensing layer 12 may comprise a first layer 16 oriented perpendicular to the axial direction 14 and a second layer 18 disposed adjacent to the first layer 16 in the axial direction 14 and in contact with the first layer 16. In certain aspects, the combined sensing layer 12 may comprise additional layers, so long as the function of the first layer 16 and second layer 18 is retained.

The first layer 16 may have a thickness in the axial direction 14 ranging from about 1 micrometer to about 1 centimeter. In certain aspects, the first layer 16 may have a thickness in the axial direction 14 of at least about 1 μm, at least about 10 μm, at least about 100 μm, at least about 1 mm, at least about 10 mm, or at least about 100 mm. In certain aspects, the first layer 16 may have a thickness in the axial direction 14 of at most about 1 cm, at most about 100 mm, at most about 10 mm, at most about 1 mm, or at most about 100 μm.

The first layer 16 may have a physical dimension perpendicular the axial direction 14 ranging from about 1 micrometer to about 1 centimeter. In certain aspects, the first layer 16 may have a physical dimension perpendicular to the axial direction 14 of at least about 1 μm, at least about 10 μm, at least about 100 μm, at least about 1 mm, at least about 10 mm, or at least about 100 mm. In certain aspects, the first layer 16 may have a physical dimension perpendicular to the axial direction 14 of at most about 1 cm, at most about 100 mm, at most about 10 mm, at most about 1 mm, or at most about 100 μm. The first layer 16 may have a physical dimension perpendicular the axial direction 14 ranging from about 1 micrometer to about 1 centimeter.

The first layer 16 may have an average surface roughness ranging from about 0.4 nm to 1000 nm in an area of 50 square micrometers. In certain aspects, the first layer 16 may have an average surface roughness of at least about 0.4 nm, at least about 1 nm, at least about 10 nm, at least about 50 nm, at least about 100 nm, or at least about 500 nm in an area of 50 square micrometers. In certain aspects, the first layer 16 may have an average surface roughness of at most about 1000 nm, at most about 750 nm, at most about 500 nm, at most about 250 nm, at most about 100 nm, or at most about 50 nm in an area of 50 square micrometers.

The second layer 18 may have a thickness in the axial direction 14 ranging from about 1 micrometer to about 1 centimeter. In certain aspects, the second layer 18 may have a thickness in the axial direction 14 of at least about 1 μm, at least about 10 μm, at least about 100 μm, at least about 1 mm, at least about 10 mm, or at least about 100 mm. In certain aspects, the second layer 18 may have a thickness in the axial direction 14 of at most about 1 cm, at most about 100 mm, at most about 10 mm, at most about 1 mm, or at most about 100 μm.

The second layer 18 may have a physical dimension perpendicular the axial direction 14 ranging from about 1 micrometer to about 1 centimeter. In certain aspects, the second layer 18 may have a physical dimension perpendicular to the axial direction 14 of at least about 1 μm, at least about 10 μm, at least about 100 μm, at least about 1 mm, at least about 10 mm, or at least about 100 mm. In certain aspects, the second layer 18 may have a physical dimension perpendicular to the axial direction 14 of at most about 1 cm, at most about 100 mm, at most about 10 mm, at most about 1 mm, or at most about 100 μm.

The second layer 18 may have an average surface roughness ranging from about 0.4 nm to 1000 nm in an area of 50 square micrometers. In certain aspects, the second layer 18 may have an average surface roughness of at least about 0.4 nm, at least about 1 nm, at least about 10 nm, at least about 50 nm, at least about 100 nm, or at least about 500 nm in an area of 50 square micrometers. In certain aspects, the second layer 18 may have an average surface roughness of at most about 1000 nm, at most about 750 nm, at most about 500 nm, at most about 250 nm, at most about 100 nm, or at most about 50 nm in an area of 50 square micrometers.

The first layer 16 may comprise or consist essentially of a first composite material. The first composite material may comprise a PPy/PMMA/PEG composite material, a PPy/PMMA composite material, PPy/PEG composite material, PMMA/PEG composite material, a PVDF-HFP composite having a plurality of carbon black particles embedded therein, a PVDF-HFP composite having a plurality of carbon black particles and a plurality of carbon nanotubes embedded therein, and combinations thereof. In certain applications, the first composite material may comprise a PPy/PMMA/PEG composite material or a PPy/PMMA composite material.

The second layer 18 may comprise or consist essentially of a second composite material. The second composite material may be different than the first composite material and may comprise a PPy/PMMA/PEG composite material, a PPy/PMMA composite material, PPy/PEG composite material, PMMA/PEG composite material, a PVDF-HFP composite having a plurality of carbon black particles embedded therein, a PVDF-HFP composite having a plurality of carbon black particles and a plurality of carbon nanotubes embedded therein, and combinations thereof. In certain applications, the second composite material is different than the first composite material and may comprise a PPy/PMMA/PEG composite material or a PPy/PMMA composite material.

The first composite material or second composite material may comprise a swellable polymer. In certain applications, the swellable polymer may exhibit a change in volume upon exposure to an analyte of interest. In certain applications, the swellable polymer is PMMA.

The first composite material or second composite material may comprise a conductive polymer. In certain applications, the conductive polymer may exhibit a change in an electronic property upon exposure to an analyte of interest. In certain applications, the change in electronic property is a change in resistance or conductivity.

The first layer 16 and second layer 18 may be configured to swell or contract in a plane perpendicular to the axial direction 14.

The combined sensing layer 12 may be restricted from swelling in the axial direction 14. Suitable means of restricting swelling in the axial direction 14 include, but are not limited to, providing a housing to restrict swelling in the axial direction 14, physically obstructing swelling in the axial direction 14, and the like.

In certain aspects, the sensing layer may comprise a plurality of resistance connections 20 sufficient to enable measurement of one or more of a first resistance of the first layer 16, a second resistance of the second layer 18, and a third resistance of the combined sensing layer 12. In certain aspects, the sensor 10 can include one or more resistance measuring circuits.

The first resistance, second resistance, and third resistance may each have distinct responses to an analyte of interest. Suitable analytes of interest are those set forth above with respect to the composite material. A change in resistance can include an increase or decrease in resistance.

The first resistance, second resistance, and third resistance may be utilized in combination to distinguish between analytes of interest. For example, a first analyte of interest may impact the first resistance and second resistance in the same fashion as a second analyte of interest, while the third resistance is impacted differently by the first and second analyte of interest. Alternatively, a first analyte of interest may impact the first resistance and third resistance in the same fashion as a second analyte of interest, while the second resistance is impacted differently by the first and second analyte of interest. In principle, so long as at least one resistance provides a unique response between two analytes of interest, the sensor 10 is capable of distinguishing between the analytes. The first resistance, second resistance, and third resistance can be used to "fingerprint" analytes of interest. In the event there are more measurable resistances with distinct responses to analytes of interest, the additional measurable resistances can also be used to "fingerprint" analytes of interest.

The first resistance, second resistance, and third resistance may be measured separately or simultaneously.

Figure 2:
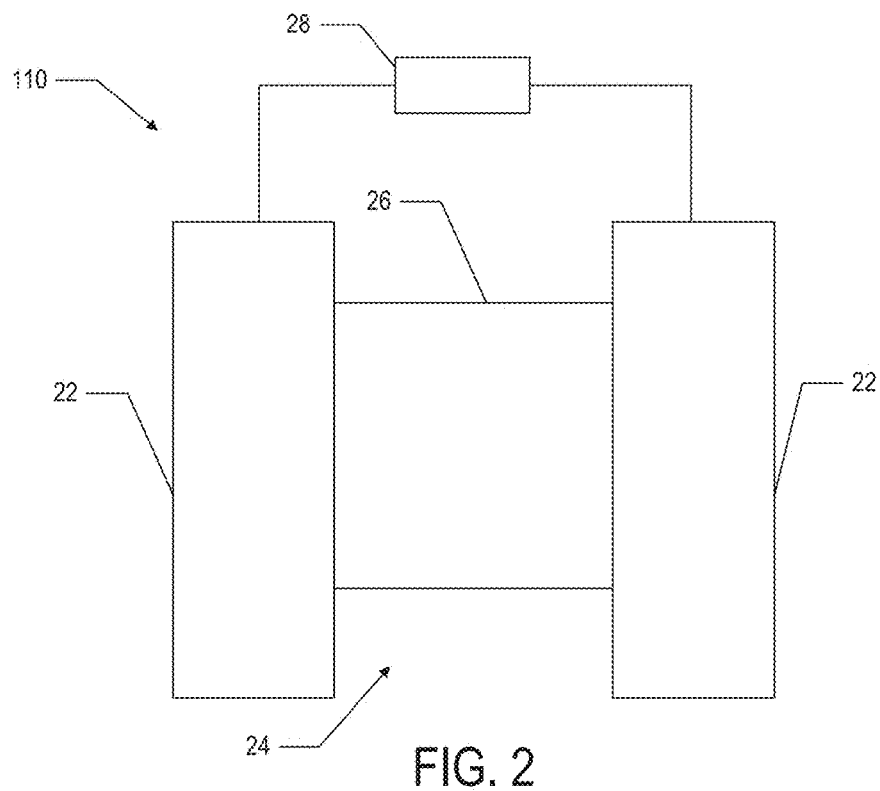
FIG. 2 is a schematic of a sensor according to one aspect of the present disclosure.
Figure 3:
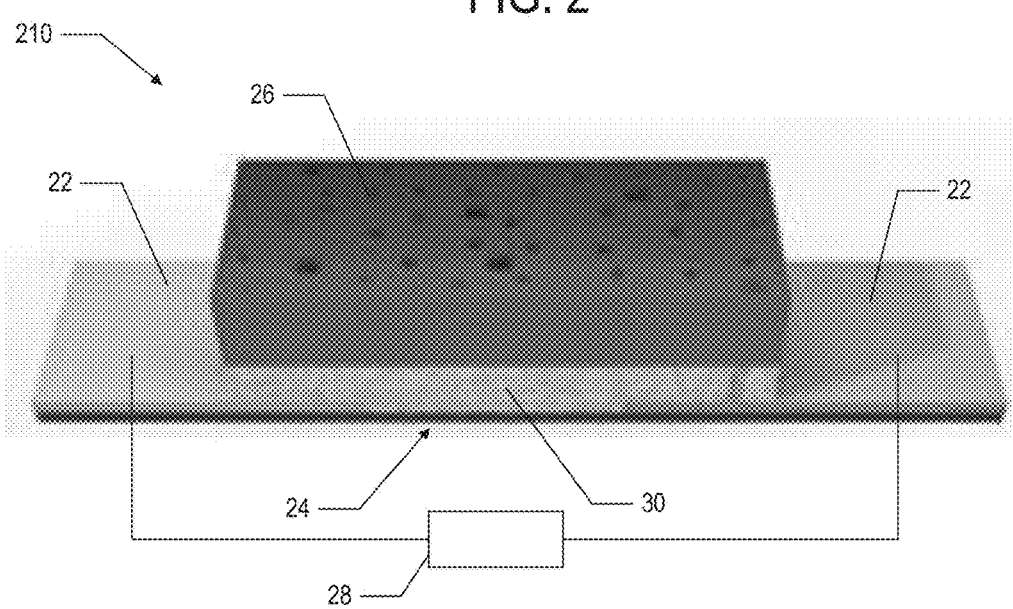
FIG. 3 is a schematic of a sensor according to one aspect of the present disclosure.

Referring to FIG. 2, in certain aspects, the sensor 110 can include two sensor electrodes 22 separated by a sensor gap 24, a composite material 26 located in the sensor gap 24 and contacting the two sensor electrodes 22, and a sensor resistance measurement circuit 28 coupled to the sensor electrodes 22 and configured to measure a change in resistance between the sensor electrodes 22. In certain aspects, the composite material 26 can cover at least part of the two sensor electrodes 22.

In certain aspects, the sensor 210 can include two sensor electrodes 22 separated by a sensor gap 24, a polymeric material 30 located in the sensor gap 24 and covering at least part of the two sensor electrodes, a composite material 26 contacting the polymeric material 30, and a resistance measurement circuit 28 coupled to the two sensor electrodes 22 and configured to measure a change in resistance between the two sensor electrodes 22.

The sensor electrodes 22 can be interdigitated electrodes. The sensor electrodes 22 can be made of a conductive material, for example, gold.

As user herein, sensor gap 24 refers to the area between the sensor electrodes 22 at a location where the sensor electrodes 22 are closest to one another. In certain aspects, the sensor electrodes 22 are spaced apart by a substantially consistent distance along the entire length of the sensor electrodes 22. In certain aspects, the sensor gap 24 can span a distance ranging from about 10 nm to about 1 mm.

In certain aspects, the composite material 26 can comprise a poly(vinylidene fluoride-hexafluoropropylene) (PVDF-HFP) composite having a plurality of carbon black particles embedded therein, a PVDF-HFP composite having a plurality of carbon black particles and a plurality of carbon nanotubes embedded therein, or a PVDF-HFP composite having a plurality of gold nanoparticles embedded therein.

In certain aspects, the composite material 26 can form a layer having a thickness ranging from about 1 mm to about 1 cm. In certain aspects, the composite material 26 can form a layer having thickness of at least about 3 mm, at least about 10 mm, at least about 100 mm, at least about 1 mm, at least about 10 mm, or at least about 100 mm. In certain aspects, the composite material 26 can form a layer having a thickness of at most about 1 cm, at most about 100 mm, at most about 10 mm, at most about 1 mm, at most about 100 mm, at most about 50 mm, or at most about 10 mm. In certain applications, the thickness is measured from the top of the electrode to the top of the layer. In certain applications, the thickness at a location within the sensor gap 24. In certain applications, the thickness is measured from the top of the polymeric material 30 to the top of the composite material 26.

In certain aspects, the PVDF-HFP composite having a plurality of carbon black particles embedded therein can have a ratio by weight of PVDF-HFP to carbon black ranging from 100:1 to 1:10.

In certain aspects, the PVDF-HFP composite having a plurality of carbon black particles and a plurality of carbon nanotubes embedded therein can have a ratio by weight of PVDF-HFP to carbon black ranging from 100:1 to 1:10. For certain applications, the PVDF-HFP composite having a plurality of carbon black particles and a plurality of carbon nanotubes embedded therein can have a ratio by weight of PVDF-HFP to carbon black of about 20:1.

In certain aspects, the PVDF-HFP composite having a plurality of carbon black particles and a plurality of carbon nanotubes embedded therein can have a ratio by weight of PVDF-HFP to carbon nanotubes ranging from 100:1 to 1:5. For certain applications, the PVDF-HFP composite having a plurality of carbon black particles and a plurality of carbon nanotubes embedded therein can have a ratio by weight of PVDF-HFP to carbon nanotubes of 2:1.

In certain aspects, the PVDF-HFP composite having a plurality of gold nanoparticles embedded therein can have a ratio by weight of PVDF-HFP to gold nanoparticles ranging from 100:1 to 1:10.

In certain aspects, the carbon black can be C65 carbon black. In certain aspects, the carbon nanotubes can be single wall carbon nanotubes.

In certain aspects, the gold nanoparticles can include a surface coating of one or more functional groups selected from the group consisting of $C_1$-$C_9$ thiol-alkanes, $C_{10}$-$C_{20}$ thiol-alkanes, $C_2$-$C_9$ thiol-aromatics, $C_{10}$-$C_{20}$ thiol-aromatics, and combinations thereof. In certain applications, the functional group can be dodecanethiol, 4-mercaptophenol, or 4-mercaptopyridine.

The resistance measurement circuit 28 can take the form of any resistance measurement device known to one of ordinary skill in the electrical arts, for example, two conductive leads and a multimeter.

In certain aspects, the polymeric material 30 can comprise PVDF-HFP, PVDF, PEG, PMMA, PPy, polyaniline, chitosan, polystyrene, polyethylene oxide, polyvinyl alcohol, or other similar polymers.

In certain applications, the composite material 26 includes as one of its components the same material as the polymeric material 30.

In certain aspects, the polymeric material 30 can form a layer having a thickness ranging from about 100 nm to about 1 mm.

IV. Sensor Systems

This disclosure provides sensor systems that can include one or more of the sensors described herein, including but not limited to, two or more, three or more, four or more, five or more sensors described herein.

In certain aspects, the sensor systems can include sensors with different sensitivities or selectivities, such that the sensor system has an overall improved sensitivity or selectivity. These different sensitivities or selectivities can be used to "fingerprint" analytes of interest.

V. Use of Sensors

This disclosure provides uses of the sensors disclosed herein. In certain aspects, the sensors disclosed herein may be used for detecting the concentration of an analyte of interest within a target fluid. Suitable analytes of interest are those set forth above with respect to the composite material.

This disclosure also provides uses of the sensors described herein. Use of the sensor may comprise exposing the sensor to a target fluid suspected of containing one or more analytes of interest. Use of the sensor may further comprise measuring the first resistance value, the second resistance value, or the third resistance value. In certain applications, use of the sensor may comprise measuring the first resistance value, the second resistance value, and the third resistance value. In aspects where further resistance values are measurable, use of the sensor may comprise measuring the further resistance values.

The target fluid may be a fluid capable of including an analyte of interest. Examples of target fluids include, but are not limited to, water, ethanol, acetone, chloroform, methanol, isoprene, ethane, pentane, 2-propanol, and alkanes, volatile organic compound, such as acetone, ethanol, water, isoprene, $NO_2$, $NH_3$, acetate acid, $CO_2$, ethane, pentane, 2-propanol, alkanes, NO, and the like.

Use of the sensor may further comprise monitoring a medical condition. Suitable medical conditions include those having signature VOC concentrations in the breath of persons having the medical condition. Examples of a medical condition include, but are not limited to, diabetes, and the like. In certain aspects, use of the sensor may further comprise estimating blood glucose levels.

EXAMPLES

Example 1. Preparing and Characterizing a PPy/PMMA/PEG Composite Material 0.5 ml distilled pyrrole (available commercially from Sigma-Aldrich was slowly added to a 0.1 g solution of polystyrene sulfonate (available commercially from Sigma-Aldrich, St. Louis, Mo.) in water with stirring to form a PPy/PSS solution. 0.5 g PMMA was dispersed in 250 ml of water and mixed with the PPy/PSS solution to form a mixture. A 2.04 g solution of ammonium persulfate (available commercially from Sigma Aldrich) in water was slowly added to the mixture with stirring. Chemical oxidative polymerization was carried out for several hours at temperatures below 5° C., and the resulting solution was filtered to collect a PPy/PMMA mixture. The PPy/PMMA composite was washed with distilled water and methanol several times, then placed in a vacuum chamber and dried at 50° C. for 24 hours to form a PPy/PMMA powder. 0.05 g of the PPy/PMMA powder was dissolved in 10 ml of chloroform and 10 micro liter PEG (molecular weight 23,586-26,069 g/mol, available commercially from Sigma Aldrich, St. Louis, Mo.) was added to the solution. This mixture in chloroform was sonicated with a rod sonicator (Branson, Digital Sonifier 450, 20 kHz, 400 W), at a power level 10% (40 W) for 1 minute and 30% (120 W) for 1 min, repeated for 3 to 5 cycles to produce a PPy/PMMA/PEG composite in chloroform. The PPy/PMMA/PEG composite in chloroform was dried in a vacuum chamber at 50° C. for 24 hours to produce a PPy/PMMA/PEG composite powder.

Figure 5:
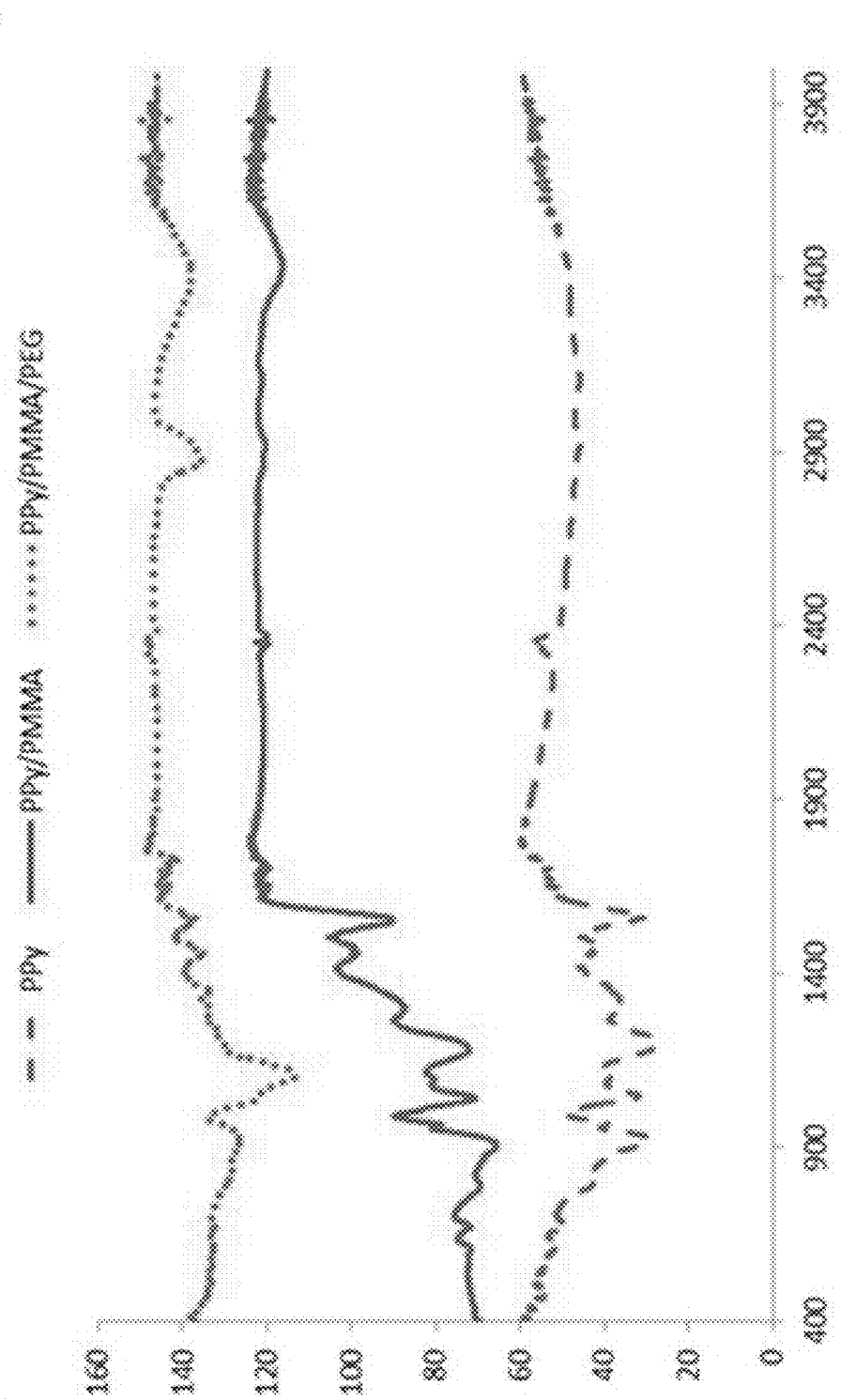
FIG. 5 shows the Fourier transform infrared spectroscopy spectra for PPy, PPy/PMMA, and PPy/PMMA/PEG.

The PPy/PMMA/PEG composite powder was characterized using Fourier transform infrared spectroscopy (FTIR). FTIR results for PPy, PPy/PMMA and PPy/PMMA/PEG are presented in FIG. 5. The absorption at 1550 $cm^{-1}$ in PPy, PPy/PMMA and PPy/PMMA/PEG is believed to be due to the —C=N and C=C ring stretching. The absorption at 1050 $cm^{-1}$ in PPy and PPy/PMMA is believed to be due to the —NH bending deformation, and it is not very clear for PPy/PMMA/PEG composite. The absorption at 950 $cm^{-1}$ is believed to be due to the —CH out of plane bending and exists in all three materials. The absorption at 3440 $cm^{-1}$ is believed to be due to C=O. The absorption at 2940 $cm^{-1}$ and 2840 $cm^{-1}$ are believed to be due to the combination of CH3 groups. The peaks at 1250 $cm^{-1}$ and 1340 $cm^{-1}$ only exists in the PPy/PMMA/PEG composite. The spectrum of PPy and PPy/PMMA composite are similar, however some variations are observed in the PPy/PMMA/PEG composite. The peak at 1370 $cm^{-1}$ seen in PPy/PMMA/PEG and it does not exist in PPy and PPy/PMMA. The peaks at 970 $cm^{-1}$ and 1080 $cm^{-1}$ in PPy and PPy/PMMA are not observed in PPy/PMMA/PEG. These results indicate a change in the bonding and formation of a new composite material with PPy/PMMA/PEG.

Figure 6:
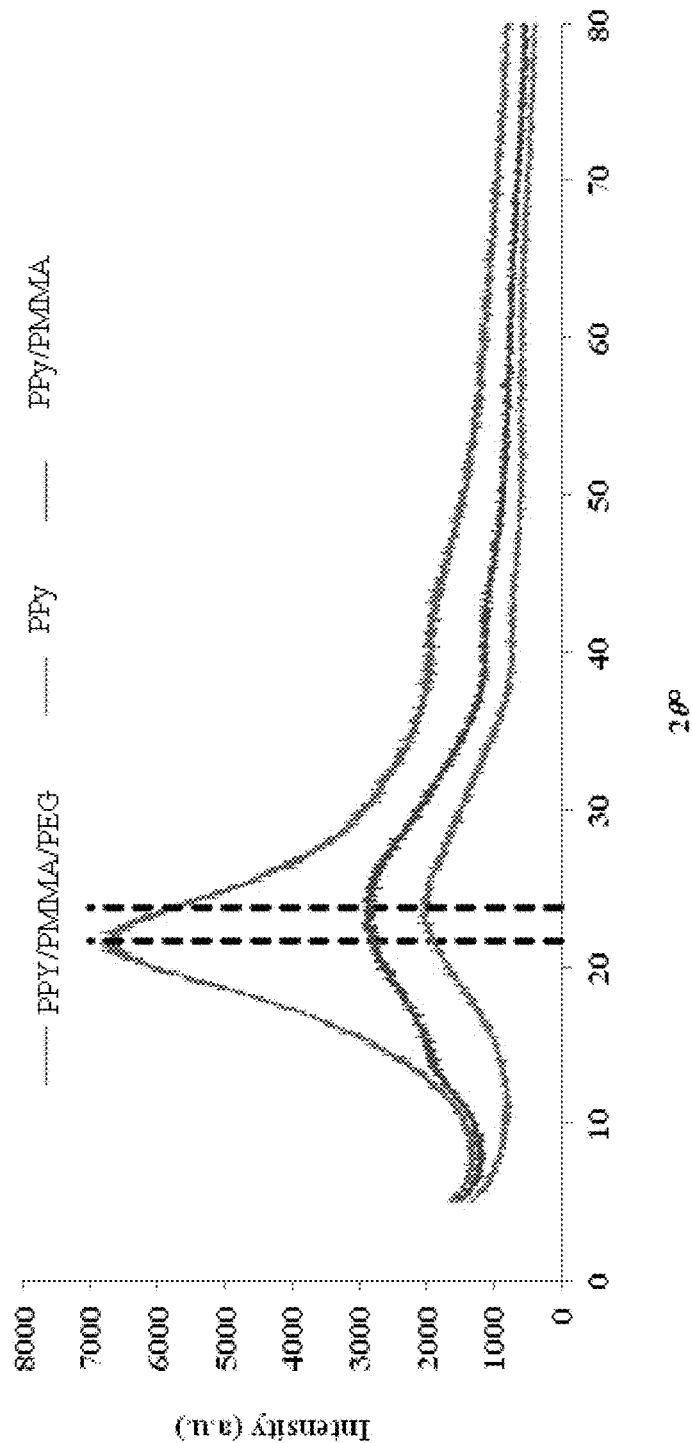
FIG. 6 shows the x-ray diffraction spectra for PPy, PPy/PMMA, and PPy/PMMA/PEG.

The PPy/PMMA/PEG composite powder was also characterized using x-ray diffraction (XRD). XRD results of PPy, PPy/PMMA, and PPY/PMMA/PEG materials are presented in FIG. 6 and Table 1. It was observed that the peaks for PPy and PPy/PMMA were at 2θ=23.53° and 23.83°, however the peak for PPy/PMMA/PEG was shifted to 2θ=21.48°. This shows stretching of crystal lattice in PPy/PMMA/PEG as compared to PPy and PPy/PMMA and indicates the formation of a new composite with PPy/PMMA/PEG.

TABLE 1

|    | PPy   | PPy/PMMA | PPy/PMMA/PEG |
|----|-------|----------|--------------|
| d  | 3.7773 | 3.7834  | 4.1334       |
| 2θ | 23.53 | 23.814   | 21.480       |

Figure 11:
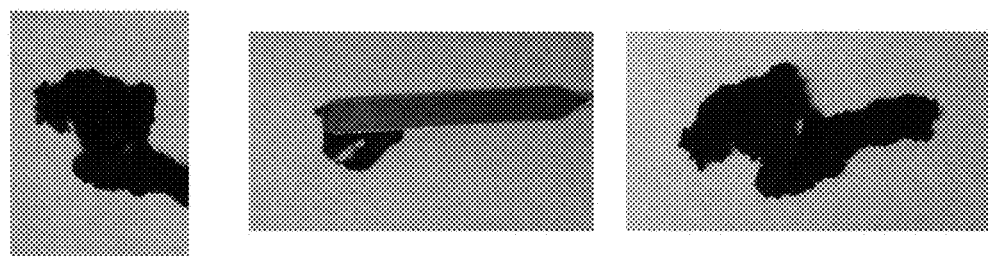
FIG. 11 shows a piece of PPy/PMMA/PEG material before bending (left), while being bent with a tool (middle), and returning to its original shape after release of the bending pressure (right).
Figure 12:
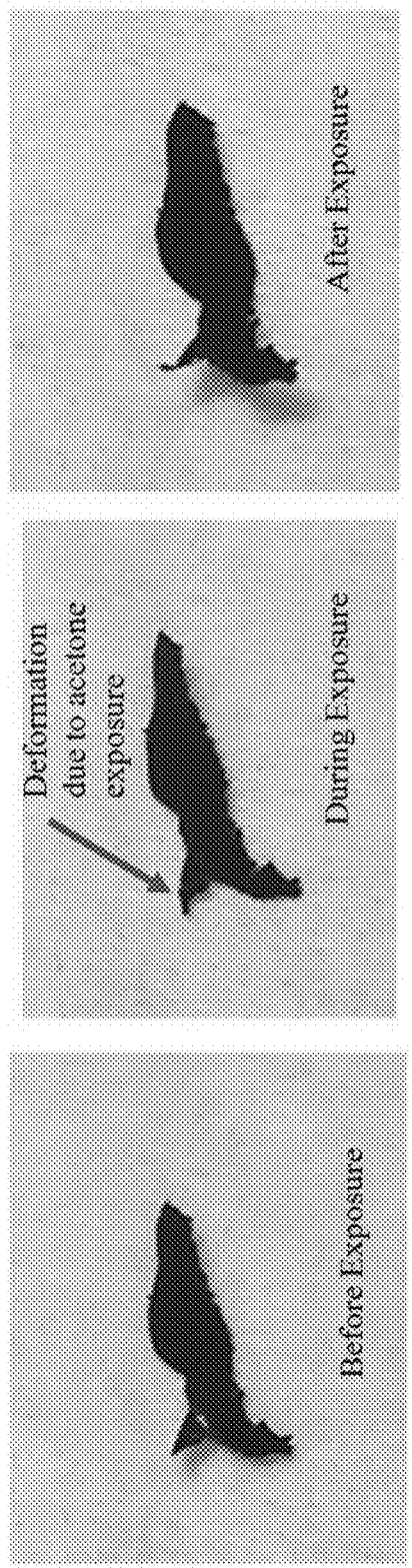
FIG. 12 shows a piece of PPy/PMMA/PEG material in open air (left), during exposure to acetone (middle), and after exposure to acetone (right).

The fabricated PPy/PMMA/PEG composite material exhibited excellent flexibility. FIG. 11 shows the PPy/PMMA/PEG composite material prior to a deformation (left), being deformed by folding and compressing with a spatula (middle), and returning to its original shape and size upon release of the spatula (right). The fabricated PPy/PMMA/PEG composite material exhibited mechanical deformation when exposed to acetone. FIG. 12 shows the PPy/PMMA/PEG composite material prior to exposure to acetone (left), during exposure to acetone (middle), and after exposure to acetone (right). Deformation was clearly exhibited during the exposure and the material returned to its original shape after exposure. This property enables the use of the disclosed material in flexible conducting applications, including flexible radio frequency shielding, flexible electronics, artificial skins, and others.

It has been shown that the addition of PEG to PMMA in addition to PPy provided the conductivity necessary to fabricate a resistive sensor, while also improving flexibility and sensitivity to acetone.

Example 2. Pellets of PPy/PMMA/PEG Composite Material

Figure 9:
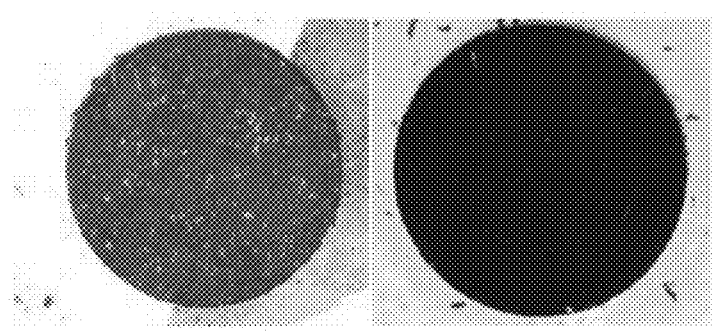
FIG. 9 shows optical images of a PPy/PMMA pellet (left) and a PPy/PMMA/PEG pellet (right).
Figure 10:
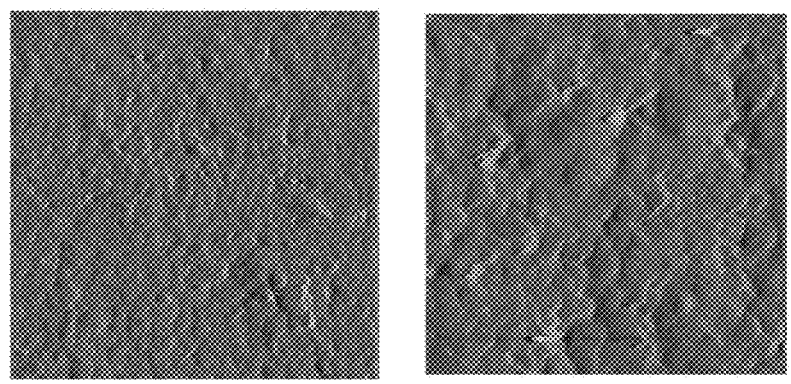
FIG. 10 shows atomic force microscopy (AFM) images of a PPy/PMMA pellet (left) and a PPy/PMMA/PEG pellet (right).

The composite materials PPy/PMMA and PPy/PMMA/PEG prepared according to Example 1 were prepared into pellets using a pellet maker and under 2000 psi at room temperature. Optical images of the pellets are shown in FIG. 9. The surfaces of the pellets were studied using atomic force microscope (AFM), and the results are shown in FIG. 10. The AFM images show that the surface roughness is on the order of tens of nanometers. This indicates that the separation between two uniform touching pellets can be less than few tens of nanometers. Decrease in the separation between two pellets up to few tens of nanometer can increase the rate of electron movements between the two pellets exponentially. The more flexible property of the PPy/PMMA/PEG composite material supports a malleable and soft contact in nanoscale range between the two pellets.

Figure 4:
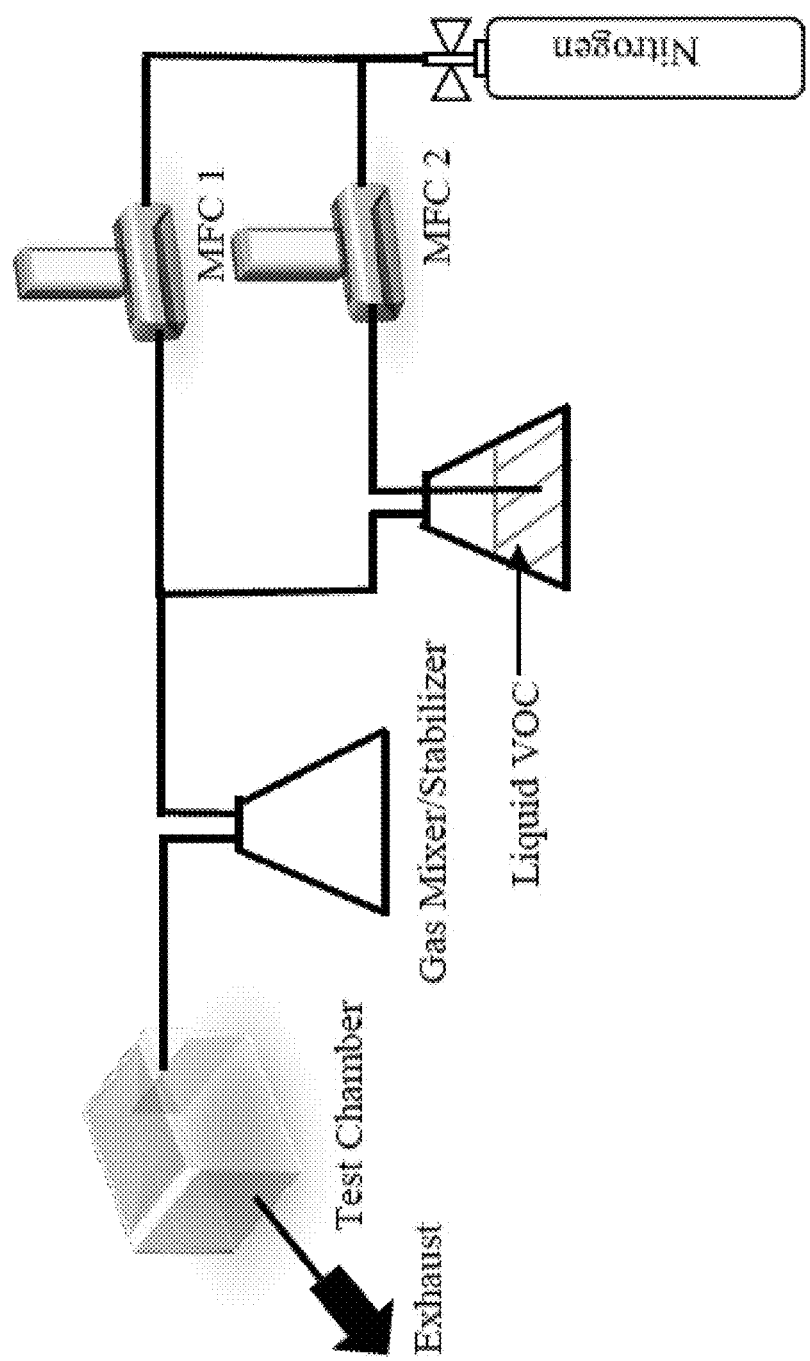
FIG. 4 is a schematic of the sensor testing setup.

The experimental setup used to measure the material and sensor response is shown in FIG. 4. Ultra high purity nitrogen (99.999% pure, available commercially from Praxair, Danbury, Conn.), at a fixed flow rate was bubbled in a liquid acetone bath in a flask and was delivered into a mixing flask with nitrogen. The concentration of acetone in the test chamber was varied by controlling the flow of nitrogen (using mass flow controllers, MFC1 and MFC2) through the acetone and pure nitrogen. The concentration of acetone for given experimental conditions and the flow rate was determined with the help of gas chromatography/mass spectroscopy (GC/MS). The mixture of acetone and nitrogen coming out of the flask was passed through a vial cooled by dry ice. The acetone trapped inside the vial was evaporated into a solid phase microextraction fiber coated with divinylbenzene/carboxen/polydimethylsiloxane (available commercially from Sigma-Aldrich, St. Louis, Mo.) and transferred to GC/MS for analysis. Based on the analysis the concentration of the acetone was calculated to be 2,900 ppm. The samples under test were placed inside the test chamber and the desired measurements were taken.

The material response to acetone was studied with the help of quartz crystal microbalance (QCM). Dilute solutions of PPy/PMMA and PPy/PMMA/PEG with the same material concentration were prepared and drop-cast on top of a 9 MHz QCM. To achieve the same mass of the deposited materials for each case, the deposition was conducted such that the change in QCM resonant frequency (measured with the help of a frequency counter) before and after the depositions are the same for all samples. The oscillation frequency of the QCM changes with the change in the mass of the material on the crystal. The relationship between the change in QCM resonant frequency ($\Delta f$) and the change in mass ($\Delta m$) on the crystal is given by eq. 1

$$\Delta f = \frac{-2f_0^2}{A\sqrt{\mu\rho}}\Delta m, \qquad (1)$$

where $f_o$ is resonant frequency, A is the area gold disk on the crystal, and $\mu$ and $\rho$ are shear modulus and density of the crystal, respectively; and all are constants. Thus, equation (1) shows the change in measured frequency is proportional to the change in mass on the crystal. When the QCM coated material is exposed to the acetone gas, the adsorption of acetone molecules onto the sensing material increases the mass, thus decreases the oscillation frequency as measured by the frequency counter. Thus the measured frequency change provides a measure for the response of the materials to the acetone.

Figure 7:
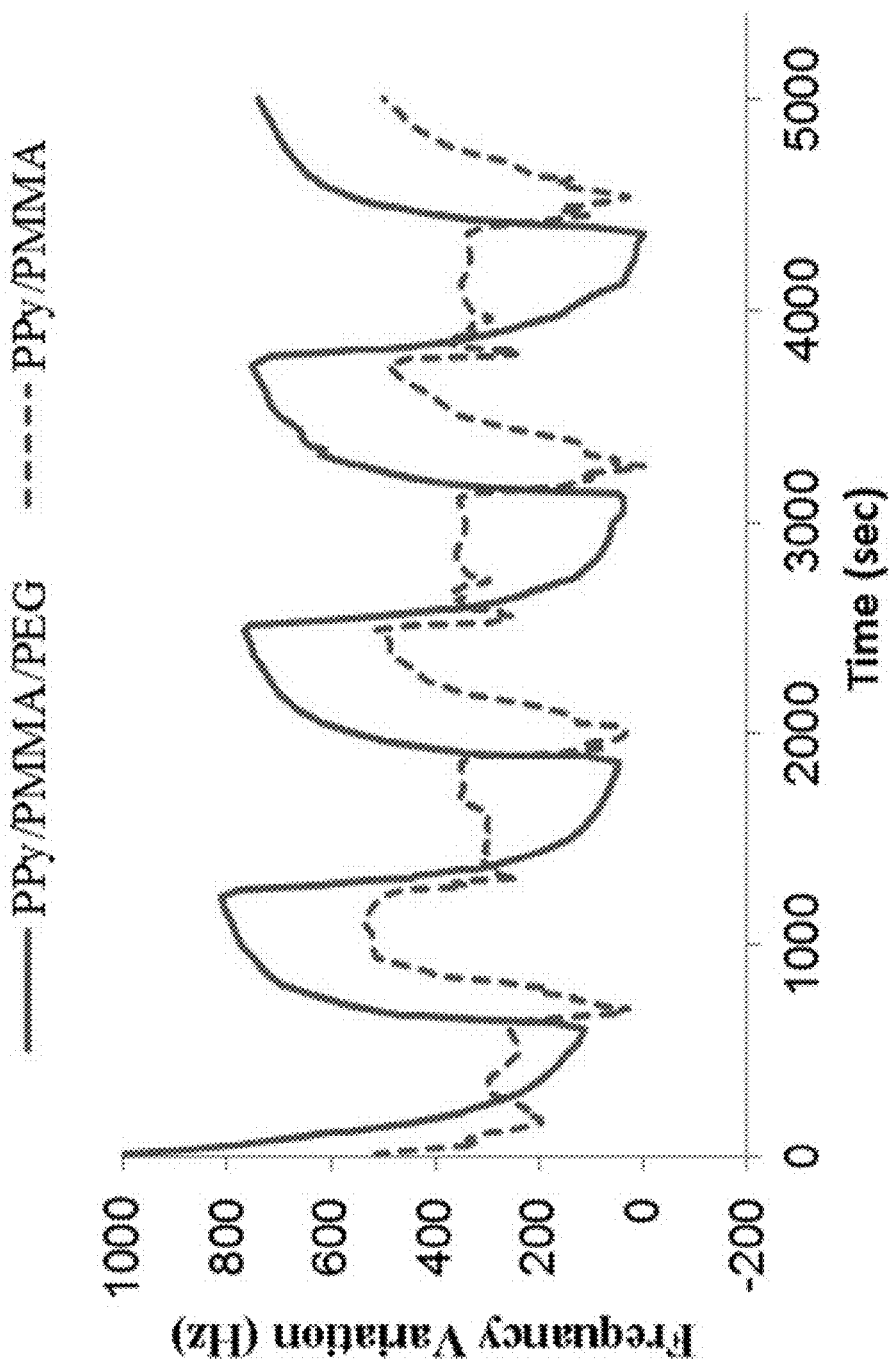
FIG. 7 shows the change in frequency of a quartz crystal microbalance (QCM) coated with PPy/PMMA/PEG and PPy/PMMA in response to acetone and nitrogen.
Figure 8:
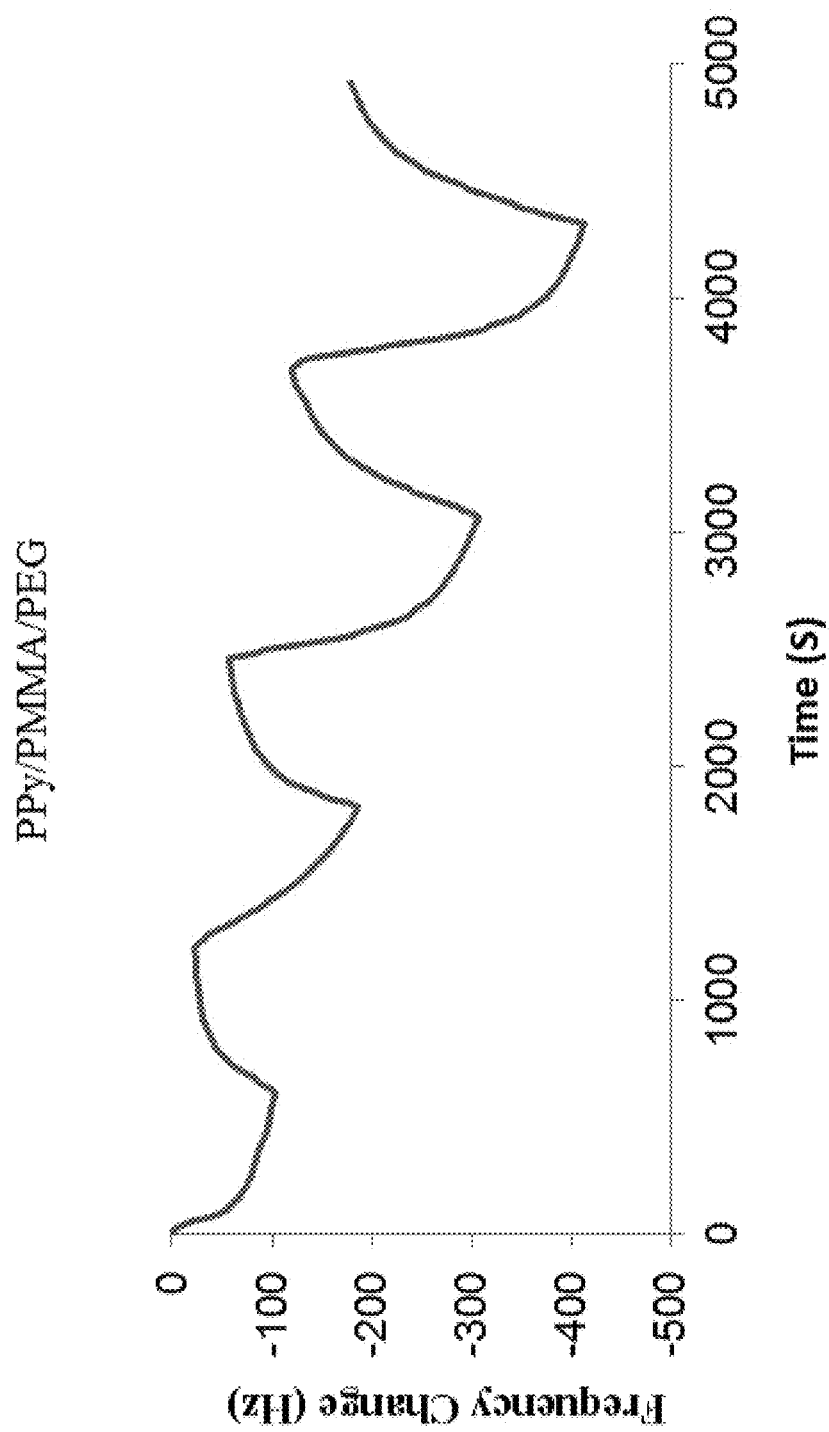
FIG. 8 shows the change in frequency of a QCM coated with PPy/PMMA/PEG in response to different concentrations of acetone.

Dilute solutions of PPy/PMMA and PPy/PMMA/PEG were on QCM and the response to acetone was measured using the setup shown in FIG. 4. The flow of gas in the chamber was fixed at 250 standard cubic centimeters per minute (SCCM). GC/MS measurement shows that bubbling of nitrogen in acetone at this rate at room normal room temperature (22° C.) and pressure produces 2990 ppm. The plot of decrease in frequency as measured by a frequency counter when acetone and nitrogen were alternately introduced, are shown in FIG. 7. As the acetone was introduced into the chamber, the acetone molecules are adsorbed onto the polymer surface increasing the total mass of the material on the QCM. This affects the oscillation frequency of the QCM as given by Eq. 1. A consistent and robust response to acetone was observed in the case of PPy/PMMA/PEG. However, in the case of the PPy/PMMA a noisier behavior attributed to the property of PPy was observed. In addition, a separate experiment conducted with PPy alone exhibited noisier response. These results also indicate the lack of composite formation between PPy and PMMA, as previously indicated by FTIR and XRD results. However, in the case PPy/PMMA/PEG, the formation of a new composite material provides a stable response. The slight downward movement of the curves with each consecutive cycle indicates the need for a longer reset time in nitrogen. From the results in FIG. 7, the time duration needed to reach to 63.2% of the final value (time constant) was calculated to be 160 s for the first acetone response, while the average for the remaining cycles was observed to be 107 s. For nitrogen the average time constant was observed to be 92.5 s. Taking into account that the setup shown in FIG. 4, with the flow rate of 250 SCCM, takes about 20 s to reach to the exposed concentration level at the sensor, it was observed that the sensor registers an average of 160 Hz change within the first 30 s. In the next set of experiment the PPy/PMMA/PEG material was exposed to various concentrations of acetone from 290 to 1160 ppm. As also indicated in FIG. 8, the first cycle was measured at 290 ppm acetone, second cycle at 580 ppm, third cycle at 870 ppm, and the fourth cycle at 1160 ppm. This was achieved by controlling the flow of nitrogen in mass flow controllers MFC1 and MFC2 as shown in FIG. 4. The respective time durations to reach to the 63.2% of the final value for acetone and nitrogen responses were observed to be 140 s and 140 s for the first cycle (290 ppm), 280 s and 140 s for the second cycle (580 ppm), 130 s and 220 s for the third cycle (870 ppm) and 150 s and 200 s for the fourth cycle (1160 ppm). It was observed that the sensor registers 18 Hz of change within first 30 s for the concentration of 290 ppm. It was also observed that the frequency did not return to the initial value at the end of the cycle for higher concentration indicating the need for a longer purge with nitrogen.

The PPy/PMMA/PEG response was stable and higher in comparison to PPy. The PPy/PMMA/PEG material was shown to detect acetone at 300 ppm.

Example 3. Sensor Device Preparation and Performance Characterization

Pellets of PPy/PMMA and PPy/PMMA/PEG prepared according to Example 2 were sandwiched to form a sensor device, shown in FIG. 1. The sensor device was then housed in a fixed casing with opening for gas inlet on two sides, towards the two pellet surfaces. The sensor housing was fixed in the vertical direction of the sensor while the pellet was free to expand in the horizontal direction. Conductivity of polypyrrole increases as it is exposed to the acetone vapor. This increases the surface conductivity of the pellet, measured as resistances R1 and R2 as shown in FIG. 1. PMMA swells as it is exposed to acetone. As the combined height of the pellets is fixed by the sensor housing, this causes the two pellets to press against each other improving the contact at the material boundary. This reduces the resistance across the two pellets. In addition, as the expansions of the pellets are inhibited in the axial direction, they slightly expand in lateral direction. This effect increases the area of the pellets and, thus, also contributes to decrease in the resistance across the pellets (R3). Swelling of the two pellets requires a bigger volume but the proposed platform is steadied with the housing and does not allow them to expand in the axial direction. This results in an increase in the pressure at the common boundary between the two pellets. This reduces the microscopic gaps (ranging from a few nanometers to a few micro meters) between the pellets and thus increases the contact area and decreases the resistance across the two pellets (R3). The resistance R3 may also be affected by quantum tunneling effects that take place across these reduced microscopic gaps.

The pellet sensor was placed in the test chamber shown in FIG. 4 and the resistances (R1, R2, and R3) were measured sequentially. Initial values of R1, R2, and R3 were measured to be 26.6 k$\Omega$, 15.9 k$\Omega$, 41.6 k$\Omega$, respectively, for a sensor that was stabilized by purging nitrogen for 20 minutes. The flow rate of gas in the chamber was fixed at 450 SCCM. For the results presented below, a bubbling rate of 450 SCCM was utilized for both acetone and ethanol. The target gas was exposed to the sensor for 35 minutes and purged with nitrogen for the next 35 minutes. Response of acetone was observed to be much faster than ethanol. Reading of the sensor output at 2 minutes into the exposure to the target gas can be used for distinguishing acetone over ethanol. Responses to acetone and ethanol at 12 minutes are summarized in Table 2. Resistances R1 and R2 were measured along PPy/PMMA and PPy/PMMA/PEG surfaces and R3 was measured across the two pellets. In Table 2, the fractional decreases in each resistance value after 12 minutes of exposure are presented. Subscript '0' represents the initial resistance value and subscript '12' represents the resistance value measured at 12 minutes of exposure to the respective gas. The response to exposure to water was also measured using the same procedure.

TABLE 2

|  | $(R1_0-R1_{12})/R1_0\%$ | $(R2_0-R2_{12})/R2_0\%$ | $(R3_0-R3_{12})/R3_0\%$ |
|---|---|---|---|
| Acetone | 81.18% | 94.85% | 86.73% |
| Ethanol | 44.14% | 32.61% | 32.10% |
| Water | 0.6085% | 0.4143% | 53.29% |

A polymer pellet based sensor for a more selective detection of acetone has been fabricated and tested. It was observed that PPy/PMMA and PPy/PMMA/PEG composites show different response characteristics with acetone and ethanol and thus the sensor provides higher selectivity for acetone over ethanol.

Example 4. Varying PEG Concentration

Figure 13:
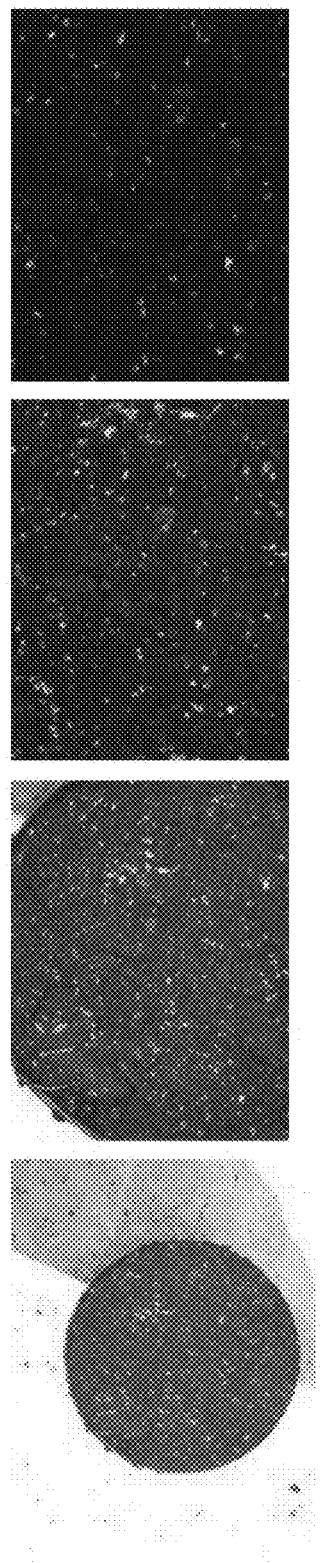
FIG. 13 shows optical images of the sample powder pellet of Example 4.
Figure 14:
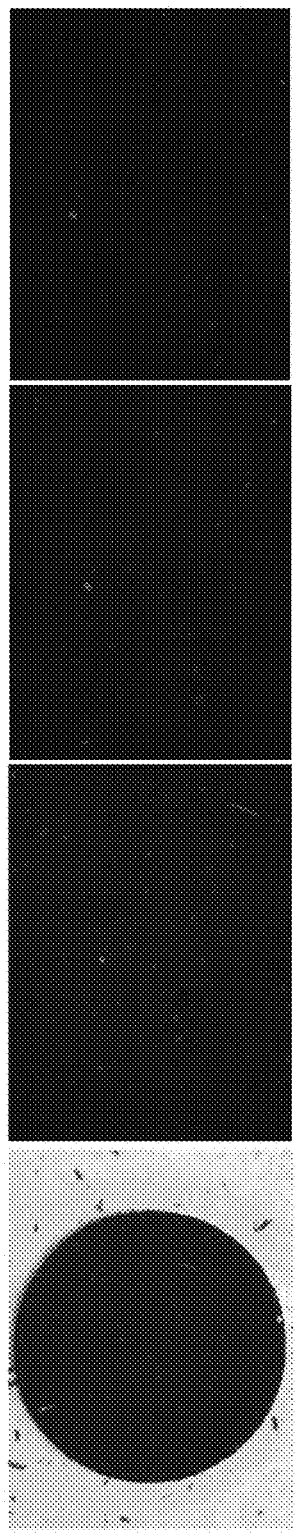
FIG. 14 shows optical images of the pellet made of the sample powder with the addition of 10 µL of PEG of Example 4.
Figure 15:
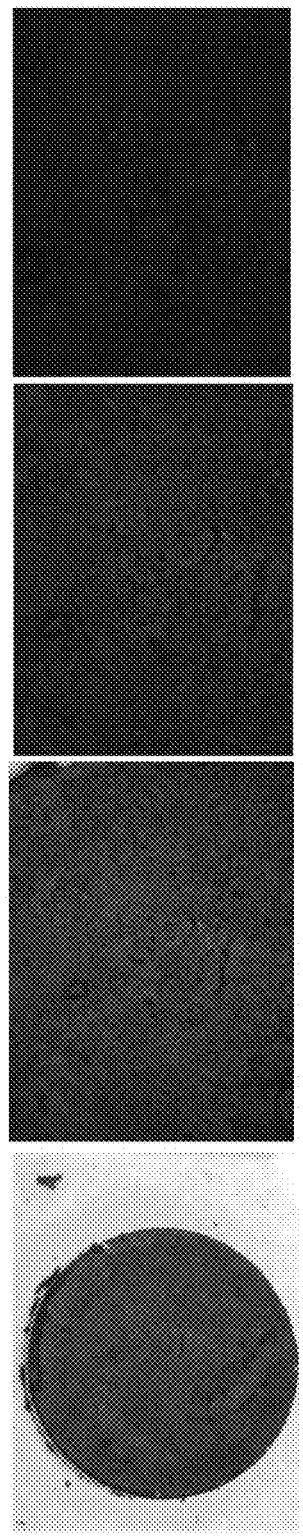
FIG. 15 shows optical images of the pellet made of the sample powder with the addition of 20 µL of PEG of Example 4.

A PPy/PMMA/PEG powder was prepared by dissolving 0.5 g pyrrole, 0.5 g PMMA, and 2 ml PEG in 200 ml of water and drying the solution overnight to form a sample powder. A portion of resulting sample powder was pressed into a pellet and optical images of the pellet are shown in FIG. 13. 0.05 g portions of the resulting sample powder were mixed with 10 μL and 20 μL of PEG in 10 ml of chloroform and dried. The resulting powders were pressed into pellets and optical images of the pellets are shown in FIG. 14 for the 10 μL of PEG and FIG. 15 for the 20 μL of PEG. Bright spots indicate the presence of isolated concentrations of PPy. The bright spots disappear as PEG concentration is increased, indicating that increasing concentrations of PEG provided a more uniform composite material.

Materials and Methods for Examples 5, 6, and 7.

Figure 16:
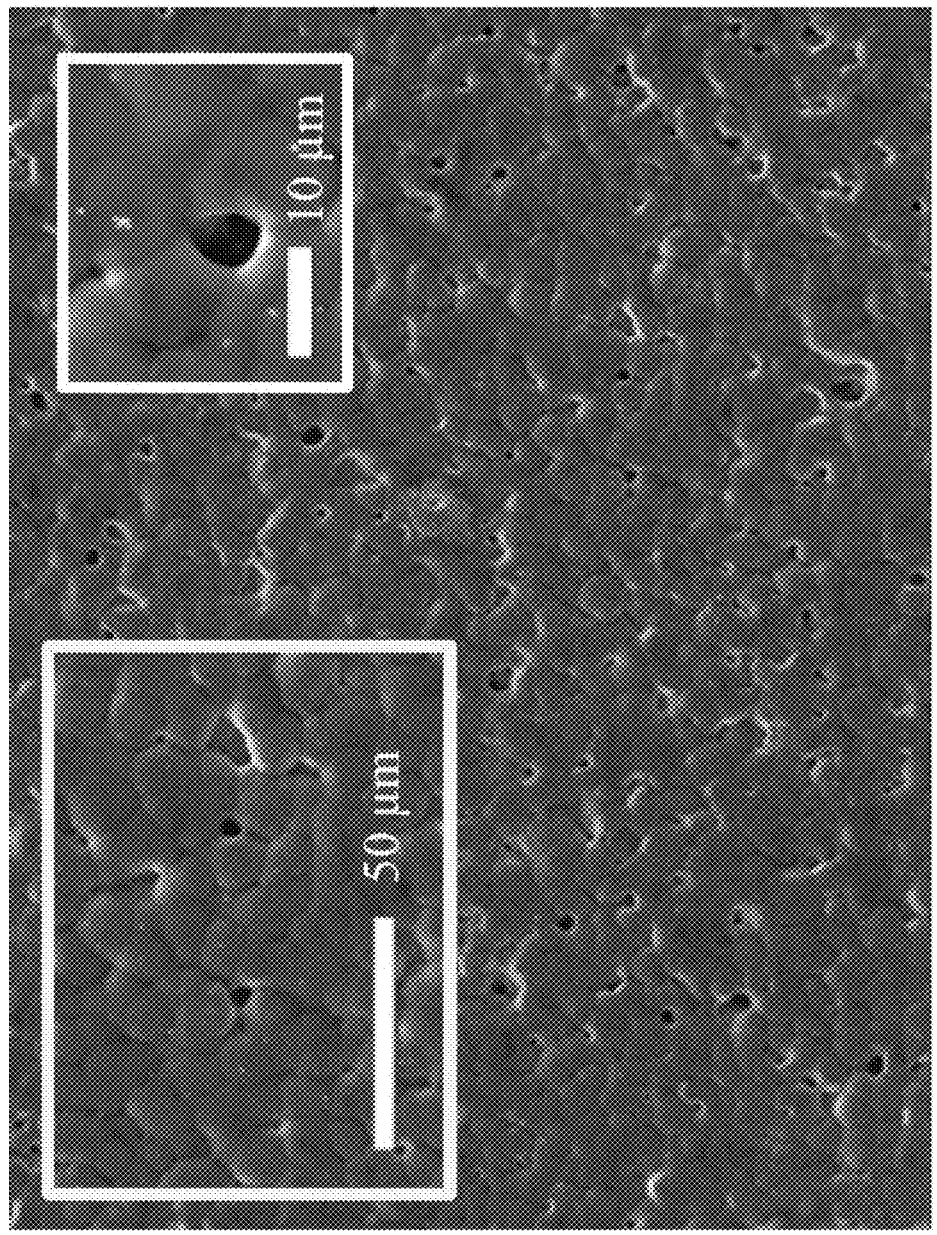
FIG. 16 shows an SEM image of a PVDF-HFP/C65/CNT composite casted over a gold-coated substrate.

Single wall CNT (HiPco) was purchased from Nanointegris, PVDF-HFP and 1-Methyl-2-pyrrolidinone (NMP) were purchased from Sigma Aldrich. Super C65 (carbon black) was obtained from Timical. The composites of PVDF-HFP/C65/CNT were formed in NMP, using the method described in L. Shi, R. Wang, Y. Cao, D. T. Liang, J. H. Tay, Effect of additives on the fabrication of poly(vinylidene fluoride-co-hexafluropropylene) (PVDF-HFP) asymmetric microporous hollow fiber membranes, J. Membr. Sci. 315 (2008) 195-204, which is incorporated herein in its entirety by reference. The product was then stirred resulting in a slurry paste. The use of a slurry paste inhibits agglomeration of CNT and C65. The slurry was either used as-is for spin coating, or further diluted for spray coating. CNT's tendency to aggregate was also observed with PVDF-HFP/CNT dissolved in NMP. The addition of super C65 within the composite inhibits CNT agglomeration and increases the uniformity of the dispersion. A field emission scanning electron microscope (SEM) image of the PVDF-HFP/C65/CNT composite (20:1:10 by wt.) drop-casted over a gold coated substrate is shown in FIG. 16. It is observed that the film is uniform across the surface, with a porous hexagonal cluster structure.

Figure 17:
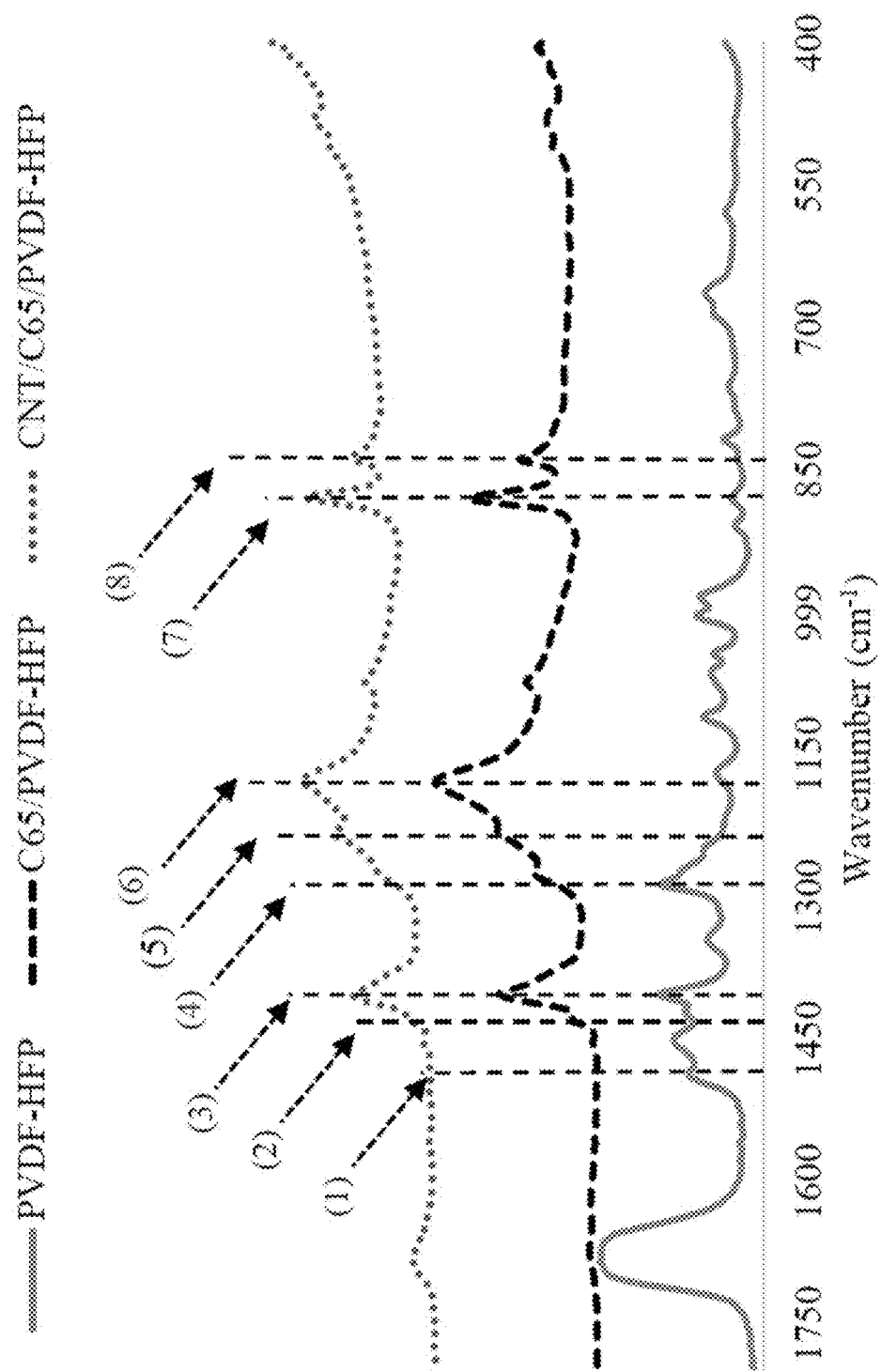
FIG. 17 shows an FTIR analysis of PVDF-HFP, PVDF-HFP/C65, and PVDF-HFP/C65/CNT composites.

FTIR analysis of PVDF-HFP, PVDF-HFP/C65 (4:11 by weight), PVDF-HFP/C65/CNT (10:1:1 by weight) are presented in FIG. 17. The results show that the crystal structure of PVDF-HFP is significantly altered in the presence of C65 and C65/CNT, indicating the formation of composite structures. PVDF-HFP exhibits peaks at 1724, 1726 and 1728 $cm^{-1}$ (stretching of the carbonyl groups), 1636 cm⁻1 (>C=O, >C=C< bonding), 1402 $cm^{-1}$ (vibrations of plasticizer), 1290 $cm^{-1}$ (—C—F— stretching vibrations), 1203 $cm^{-1}$ (asymmetrical stretching vibrations of the $CF_2$ group), 1148 $cm^{-1}$ (symmetrical stretching mode of CF), 1062 cm⁻1 (—$CF_2$— stretching vibration), 879 $cm^{-1}$ ($CF_2$ symmetric stretching) and 839 $cm^{-1}$ ($CH_2$ rocking). The vibrations at 839 and 880 $cm^{-1}$ are more distinct in PVDF-HFP/C65 composite than PVDF-HFP. This indicates a more amorphous structure for the composite since these two bands are associated with the amorphous structure of PVDF-HFP. The frequencies at 1344, 1170 (C=O), 1002, 983 (alpha phase crystal structure), 817 and 761 $cm^{-1}$ (alpha phase crystal structure) disappear in the PVDF-HFP/C65 composite and the peaks at 1062 and 516 $cm^{-1}$ shift to 1072 and 508 $cm^{-1}$, respectively. These phenomena indicate the presence of a polymer-plasticizer interaction. Insertion of CNT into the composite further modifies the structure. The new, but small, absorptions at 510 and 481 $cm^{-1}$ (beta phase crystal structure) also demonstrate changes in the crystalline structure and polarity of the composite. The changes in polar properties of the composite change its sensing characteristics to different VOCs. Ultraviolet (UV) light, infrared (IR), and oxygen plasma treatment alters the hydrophobicity of PVDF-HFP by creating oxygenated cites. These phenomena can be utilized for further fine tune the properties of sensors.

Interdigitated electrodes (IDE) of gold over silicon oxide were fabricated using a standard photolithography process. The spacing between the two electrodes was measured to be 25 μm. Spray coating and spin coating fabrication methods were used to cast films over the electrodes. For spray coating, diluted solutions of the materials were sprayed onto the IDE. The spray process was continued until a desired resistance for the film was achieved. For spin coating, a slurry solution of the materials was used. A small amount of the slurry was casted onto the IDE, which was mounted on a spin-coater. It was then spun at a high speed to achieve a desired film thickness. Next the film was dried in a vacuum oven. Three types of sensors were fabricated as described below.

Sensors were tested using the experimental setup illustrated in FIG. 4. Nitrogen (99.99% pure), at a fixed flow rate, was bubbled through liquid acetone in a flask. This nitrogen/acetone gas was diluted with pure nitrogen using a mixing flask. The concentration of acetone in the test chamber was varied by controlling the flow of nitrogen (using mass flow controllers, MFC1 and MFC2) through the acetone and pure nitrogen. The concentration of acetone for given experimental conditions and the flow rate was determined through gas chromatography/mass spectroscopy (GC/MS). The mixture of acetone and nitrogen coming out of the flask was passed through a vial cooled by dry ice. The acetone trapped inside the vial was evaporated onto a solid phase micro-extraction fiber and transferred to GC/MS for analysis. The samples under scrutiny were placed inside the test chamber and the desired measurements were taken. The same process was utilized for testing water, ethanol, and isoprene; except isoprene was kept at 2.5° C. while all other liquid VOCs were kept at room temperature.

Responses of the materials to various VOCs were studied using a quartz crystal microbalance (QCM). Dilute solutions of materials were prepared and drop-casted on top of a 9 MHz (resonant frequency) QCM. The resonant frequency of the QCM changes with the change in the mass of the material on the crystal. The relationship between the change in QCM resonant frequency (Δf) and the change in mass (Δm) on the crystal is given by equation (1).

Carboxylic-functionalized single wall CNTs (CNT-COOH) have been widely used to detect acetone. Thus, in the first step, CNT-COOH were coated over QCM and tested for acetone. It was observed that exposure to acetone registers a 220 Hz change in frequency. However, the same sensor exhibited an 877 Hz change in frequency when exposed to moisture. This is exorbitant at 2.2 times higher than the acetone response. In a similar experiment with PVDF-HFP/C65/CNT composite, it exhibited a 1635 Hz change with acetone and a 106 Hz change with water, a 15.4 times higher response to acetone than water. This represents a significant improvement in acetone selectivity over water compared to existing sensors, which is a critical aspect for breath sensor applications. These QCM results give us insight into how well the target gases are adsorbed onto the sensing materials.

Figure 18:
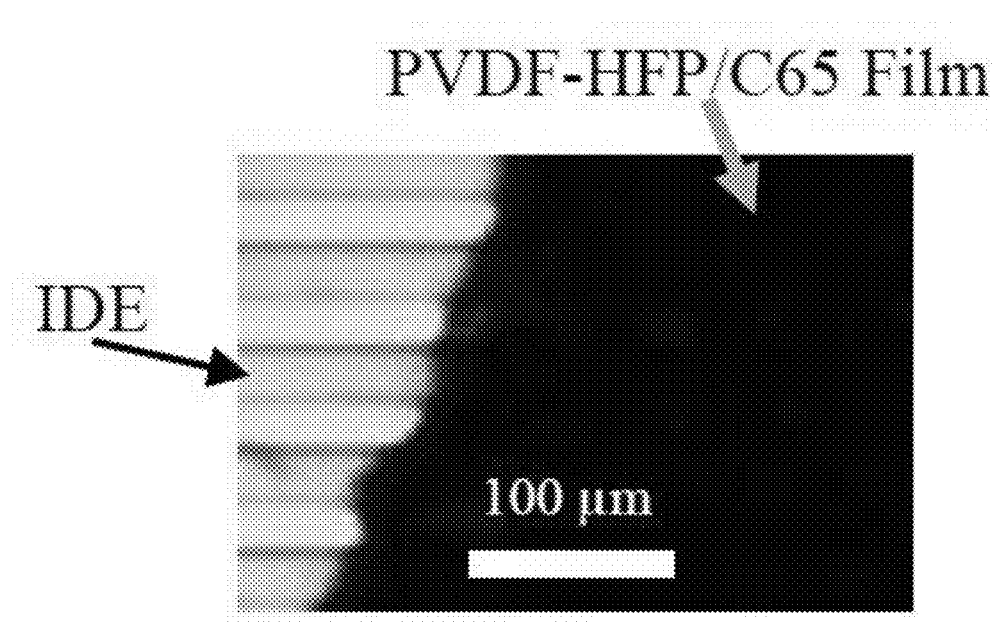
FIG. 18 is an optical image of an edge of a PVDF-HFP/C65 film deposited over interdigitated electrodes, as described in Example 5.

Example 5. Fabricating and Testing a Sensor-1 Including a PVDF-HFP/Carbon Black Composite Material Sensor-1 consists of a spray coated layer of PVDF-HFP/C65 film over the IDE. A PVDF-HFP and C65 composite dispersed in NMP was prepared and spray coating was conducted as described in the Materials and Methods section above. In the spray coating process, the film was inspected under an optical microscope and the resistance was measured after each deposition. It was observed that the C65 forms a patchy network at the beginning and, after each additional layer, slowly changes to a continuous network supported by PVDF-HFP. An optical image of an edge of a PVDF-HFP/C65 film over IDE is shown in FIG. 18. The resistance of the completed device was 864Ω. When exposed to the target VOC, the swelling of PVDF-HFP weakens the C65 network, thus increasing the resistance measured across the electrodes.

Figure 19:
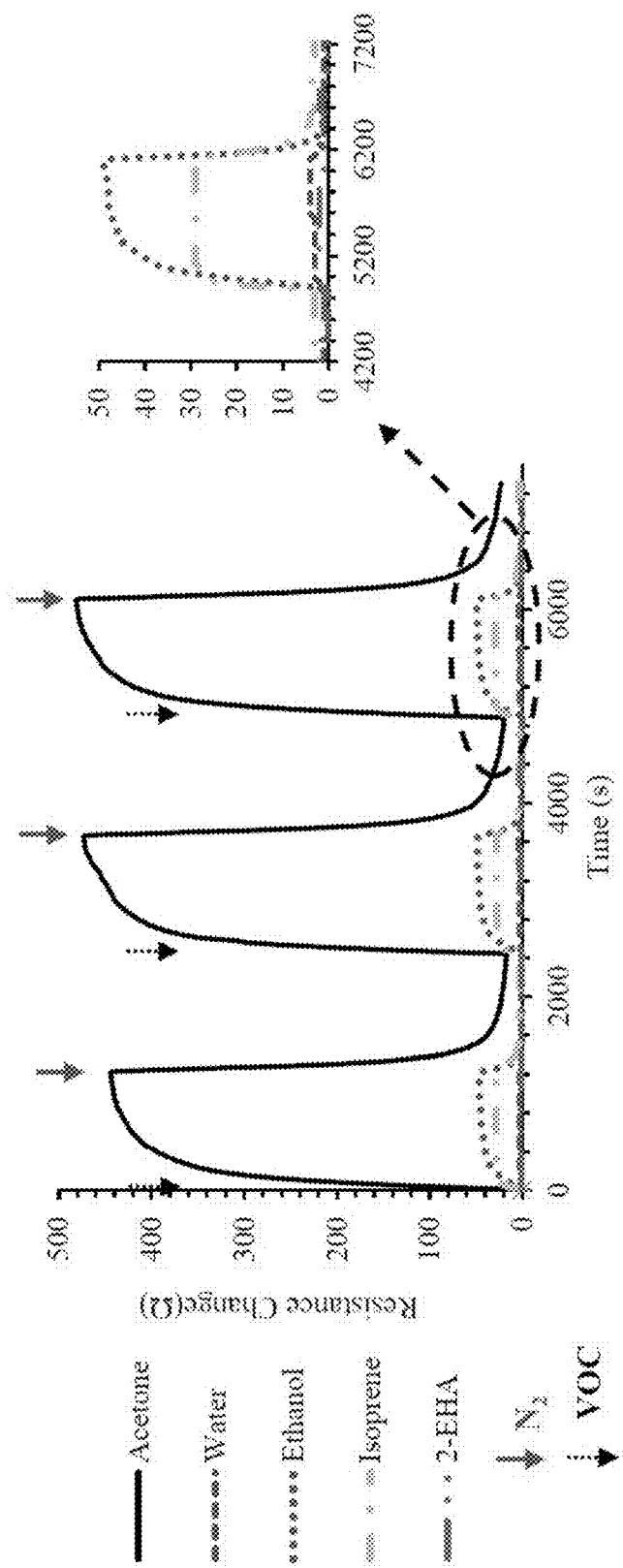
FIG. 19 shows the change in resistance of Sensor-1 of Example 5 in response to exposure to acetone, water, ethanol, isoprene, and 2-EHA.
Figure 20:
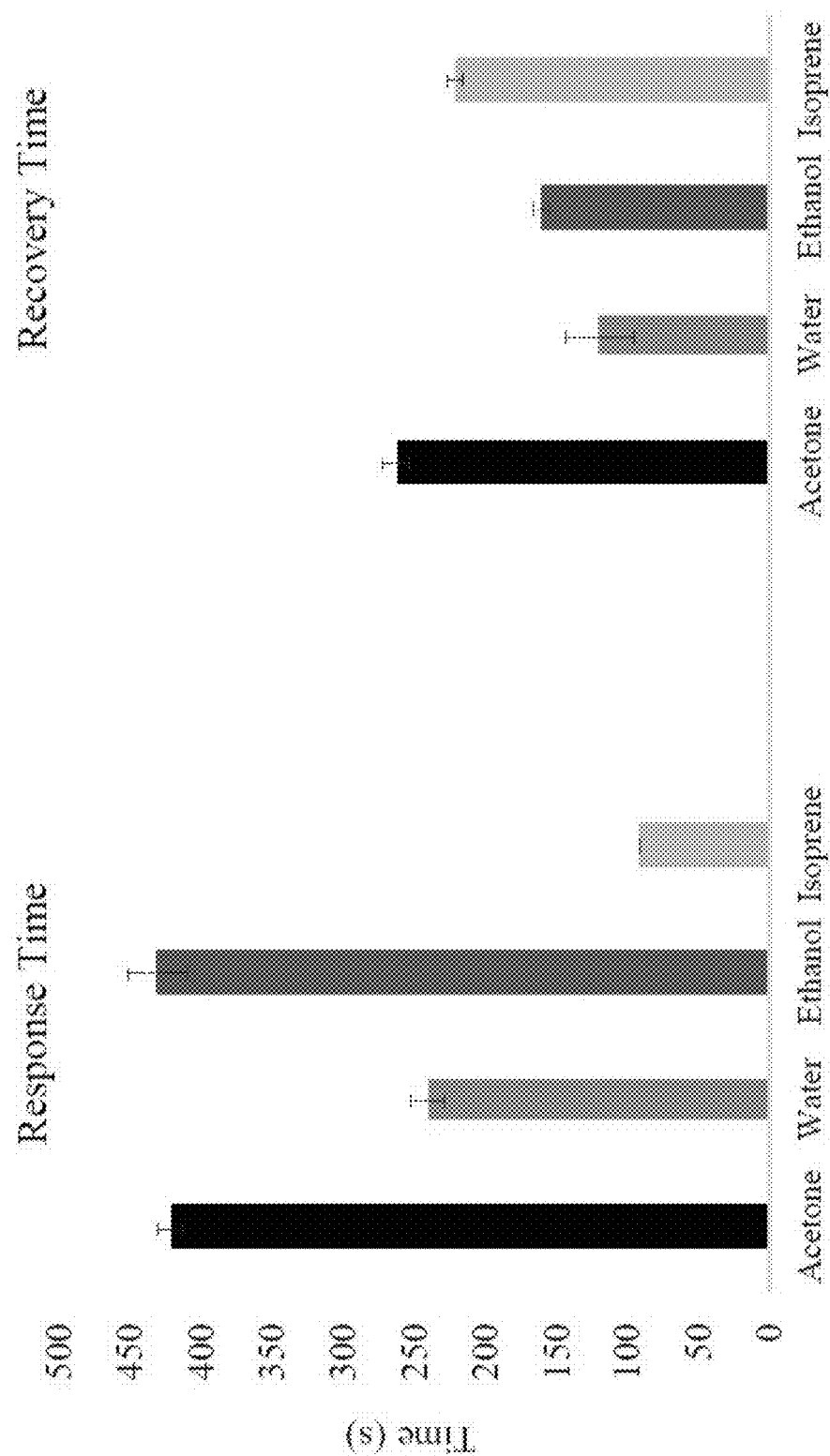
FIG. 20 shows the response and recovery times for Sensor-1 of Example 5 when exposed to acetone, water, ethanol, and isoprene.

A PVDF-HFP/C65 composite sensor fabricated on gold IDE (Sensor-1) was tested with acetone, water, ethanol, isoprene, and 2-EHA VOCs using the setup shown in FIG. 4. The resistance of the IDE after deposition of PVDF-HFP/C65 was measured to be 864Ω. The sensor was exposed to a VOC and nitrogen, each for 20 minutes. The flow of gas in the chamber was fixed at 200 standard cubic centimeters per minute (SCCM) at 22° C. Water, ethanol, isoprene, and 2-EHA were also introduced into the chamber using the above described parameters, except that isoprene was kept at 2.5° C. GC/MS measurements showed the concentration of acetone, ethanol, isoprene and 2-EHA was 44500 ppm, 10000 ppm, 50500 ppm and 248 ppm, respectively. The concentration of water (measured by a humidity sensor) was 6000 ppm. The measured resistances for the VOCs for three consecutive cycles are shown in FIG. 19. For further clarity, the plots without acetone are shown in the inset. As the VOCs are introduced into the chamber the molecules are adsorbed onto the sensor, increasing the effective resistance of the sensor. This is caused by two competing factors as described in the methods section. The swelling of PVDF-HFP matrix increases the overall resistance of the film, while the resistance of a C65 cluster decreases when the VOCs are adsorbed. The sensor exhibited a 52.6% increase in resistance when exposed to acetone, while the change was less than 0.34% for water. The resistance change for acetone is 150 times larger than that of water. Resistance changes for ethanol, isoprene, and ethyl acetate were 5.6%, 3%, and 0.11%, respectively. It is observed that the interactions of the VOCs and sensor were reversible over the three cycles. The response and recovery times (time to reach 90% of the saturation value) for the VOCs are presented in FIG. 20. The standard deviations (σ) of the three cycles are also indicated in the figure. The sensor response to isoprene is faster (90 s) compared to that of ethanol and acetone (430 s and 450 s).

Example 6. Fabricating and Testing a Sensor-2 Including a Polymer Layer and a PVDF-HFP/Carbon Black Composite Material Layer Sensor-2 is composed of two layers, a PVDF-HFP layer and a PVDF-HFP/C65 layer. A thin layer of PVDF-HFP was deposited over the IDE via spin coating. This film covers both the gold electrodes and the gap in between, and forms the first layer. Then the PVDF-HFP/C65 composite deposited over the first layer forms the second layer. SEM image of a PVDF-HFP/C65 film is shown in FIG. 21(b). The resistance of the sensor after vacuum drying was measured 3.04 kΩ. A representative schematic of the sensor is shown in FIG. 21(a). An equivalent circuit for the sensor can be considered as the resistances across PVDF-HFP layer ($R_G$) and resistance of PVDF-HFP/C65 ($R_{CP}$), also indicated in FIG. 19(a), placed in series. While the two layers were deposited separately, the second layer material may penetrate through the first layer forming vertical connections. This resulted in a less than expected overall resistance for the sensor. Interaction of the target gas with PVDF-HFP increases the volume of the polymer. Swelling of PVDF-HFP thin layer (bottom layer), increases the separation between the gold electrode and the conductive composite (top layer). This results in an increase in resistance $R_G$. Swelling of PVDF-HFP in the composite also increases the resistance of $R_{CP}$. The overall response of the sensor represents the sum of these two responses, and resulted in increased sensitivity. As these two layers respond differently with each of the VOCs, the selectivity of the sensor is enhanced. By adjusting thickness and other properties of these layers, selectivity to the presented and other VOCs can be further tuned. For example, if the first (bottom) layer is PMMA and the second (top) layer is PVDF-HFP/C65, as PVDF-HFP is more hydrophobic and more sensitive to acetone than PMMA, the increase in thickness for the first PVDF-HFP/C65 layer will cause the overall response of the sensor to decrease for water and increase for acetone. Thus, making the sensor more selective towards acetone.

Figure 22:
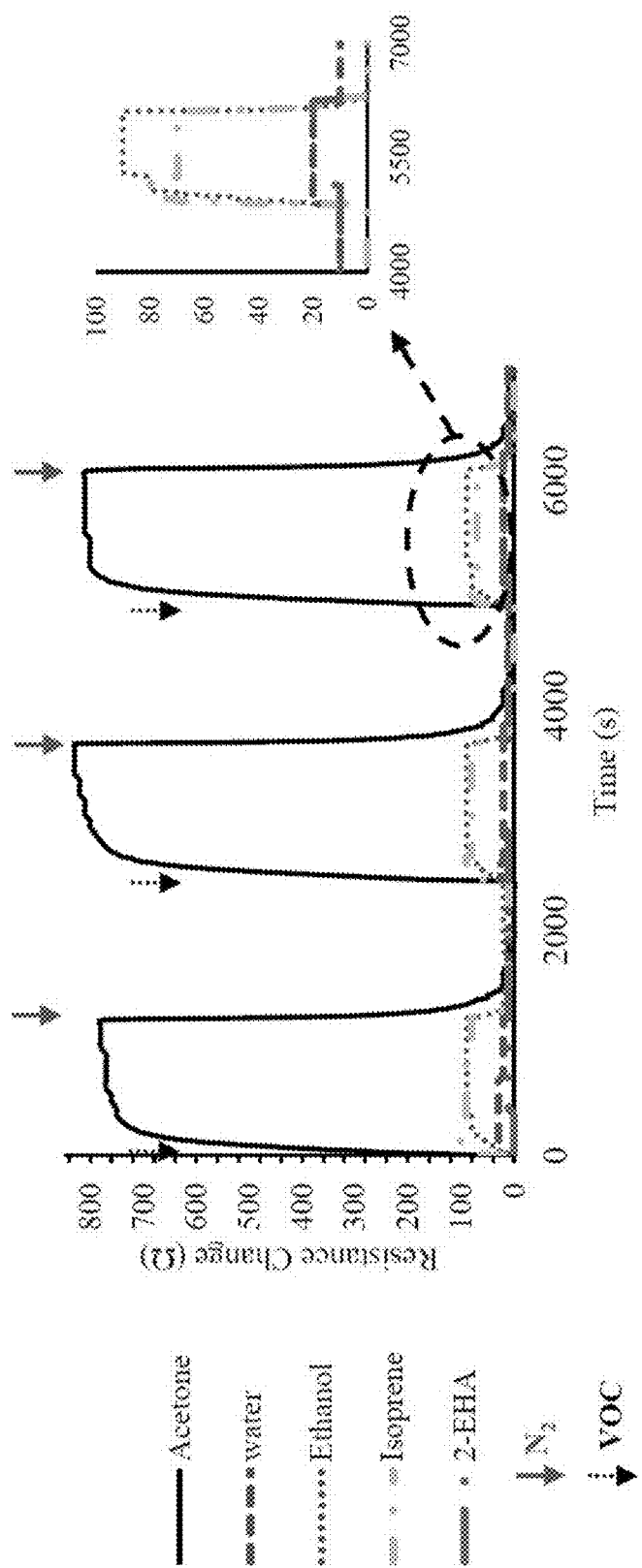
FIG. 22 shows the change in resistance of Sensor-2 of Example 6 in response to exposure to acetone, water, ethanol, isoprene, and 2-EHA.
Figure 23:
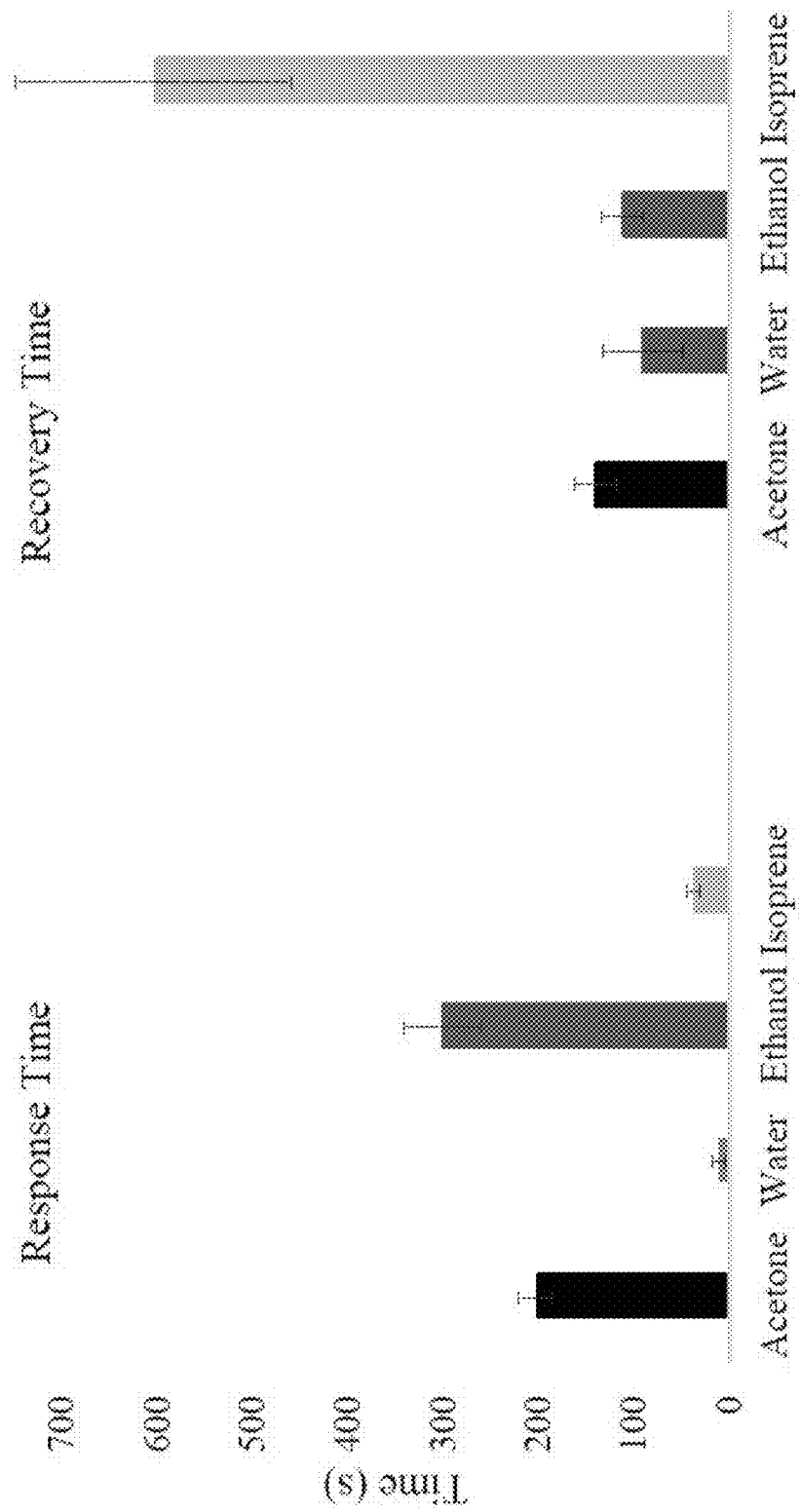
FIG. 23 shows the response and recovery times of Sensor-2 of Example 6 when exposed to acetone, water, ethanol, and isoprene.

Sensor-2 consists of overlaid layers of PVDF-HFP and PVDF-HFP/C65. The resistance of the resulting sensor was measured 3.04 kΩ. The sensor was tested with VOCs using the measurement set-up as described for Sensor-1. The resistances measured for acetone, water, ethanol, isoprene, and 2-EHA for three consecutive cycles are shown in FIG. 22. For further clarity, the plots without acetone are shown in the inset. The changes in resistance were 26.23% for acetone, 0.32% for water, 2.6% for ethanol, 2.29% for isoprene, and 0.32% for 2-EHA. The two-layer design exhibits improved responses to VOCs than other considered sensor designs. The response and recovery times (presented in FIG. 23) are improved compare to Sensor-1. The sensor response time to acetone is 200 s (compared to 420 s for Sensor-1), 20 s to water (compared to 200 s for Sensor-1), 300 s to ethanol (compared to 430 s for Sensor-1) and 35 s to isoprene (compared to 90 s for Sensor-1). Additionally, a wide range of polymers can be selected to form the first layer of the sensor design (Sensor-2), which provides a tool to further customize the sensor. This feature can be used to generate an array of sensors and improve the selectivity of the system.

Figure 24A:
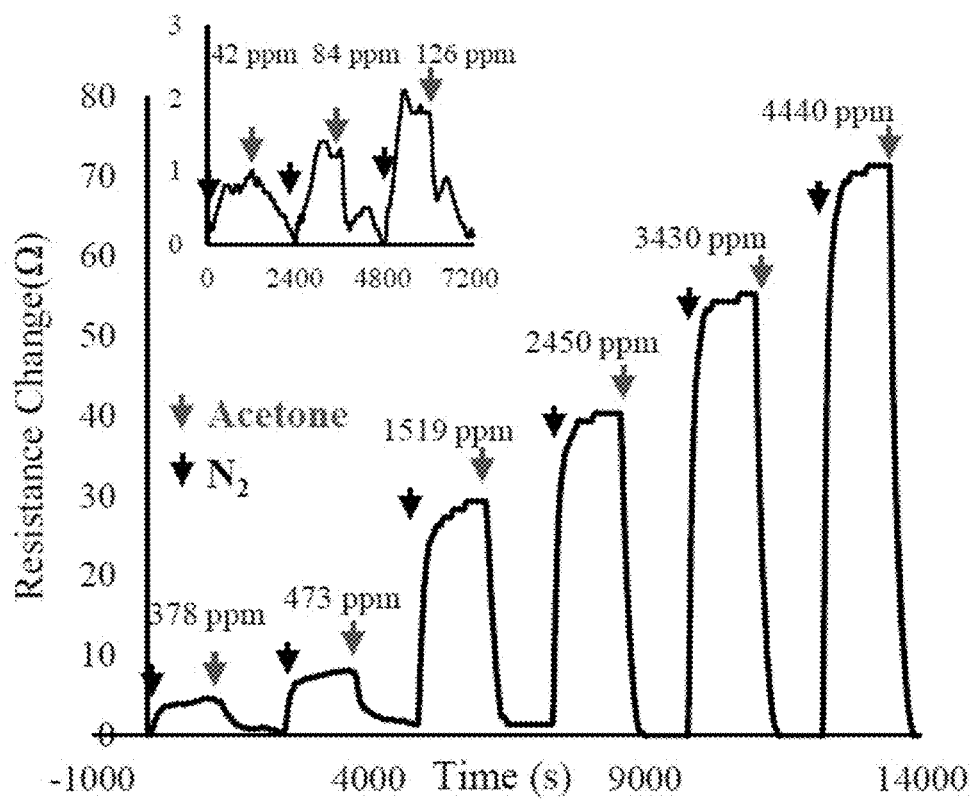
FIG. 24(a) shows the change in resistance of Sensor-2 of Example 6 in response to various concentrations of acetone.
Figure 24B:
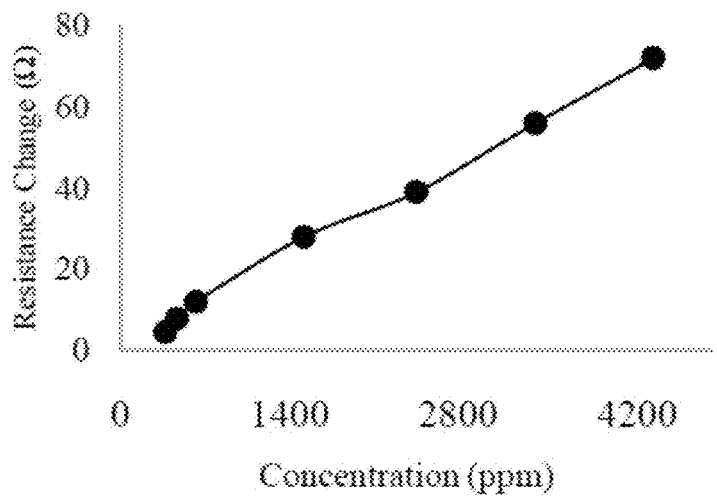
FIG. 24(b) shows the change in resistance of Sensor-2 of Example 6 in response to various concentrations of acetone.

Sensor-2 was also tested with a varying concentration of acetone, from 42 ppm to 4440 ppm. As shown in FIG. 24(a), the resistance of the sensor increases as the concentration of acetone is increased stepwise. A plot of change in resistance versus the concentration of acetone is shown FIG. 24(b). A linear relation between the resistance change and gas concentration was observed. The sensor response for a lower concentration of acetone is shown in the inset of FIG. 24(a). The resistance changes by 1Ω when exposed to 42 ppm acetone. For these lower concentration of acetone, the measured resistance was observed to fluctuate due to competing effect between swelling of PVDF-HFP (increase in resistance) and increased conductivity C65 (decrease in resistance). However, the overall resistance of the sensor increases when exposed to acetone. As the swelling (of PVDF-HFP) becomes more dominant with increasing concentration of acetone, this effect was not observed at higher concentration measurements.

Example 7. Fabricating and Testing a Sensor-3 Including a PVDF-HFP/Carbon Black/Carbon Nanotube Composite Material For Sensor-3, the composite of PVDF-HFP/C65/CNT was prepared as described above, in the Materials and Methods section, and spin coated over an IDE. The film was then dried in a vacuum oven. SEM image of the surface of the film is shown FIG. 21(c). It was observed that the CNT and C65 form a continuous network supported by the PVDF-HFP matrix. The lateral resistance path of the film is the sum of resistances due to CNT/C65 clusters ($R_C$) in the PVDF-HFP matrix and the matrix itself ($R_M$). When exposed to a VOC, the swelling of PVDF-HFP increases the resistance of the network (RM), which is caused by increased separation between the nanoparticles. On the other hand, the resistance of CNT, and thus in turn $R_C$, decrease when exposed to the VOCs. Each of the two sensing probes has a different role in the sensing mechanism of different VOCs. For example, with acetone, swelling of PVDF-HFP is more dominant; however, water does not stimulate PVDF-HFP as much as it increases the conductance of CNT/C65 clusters. This results in a phenomenon where the resistance across the two electrodes decreases when exposed to water and increases when exposed to acetone, ethanol and isoprene.

Figure 25:
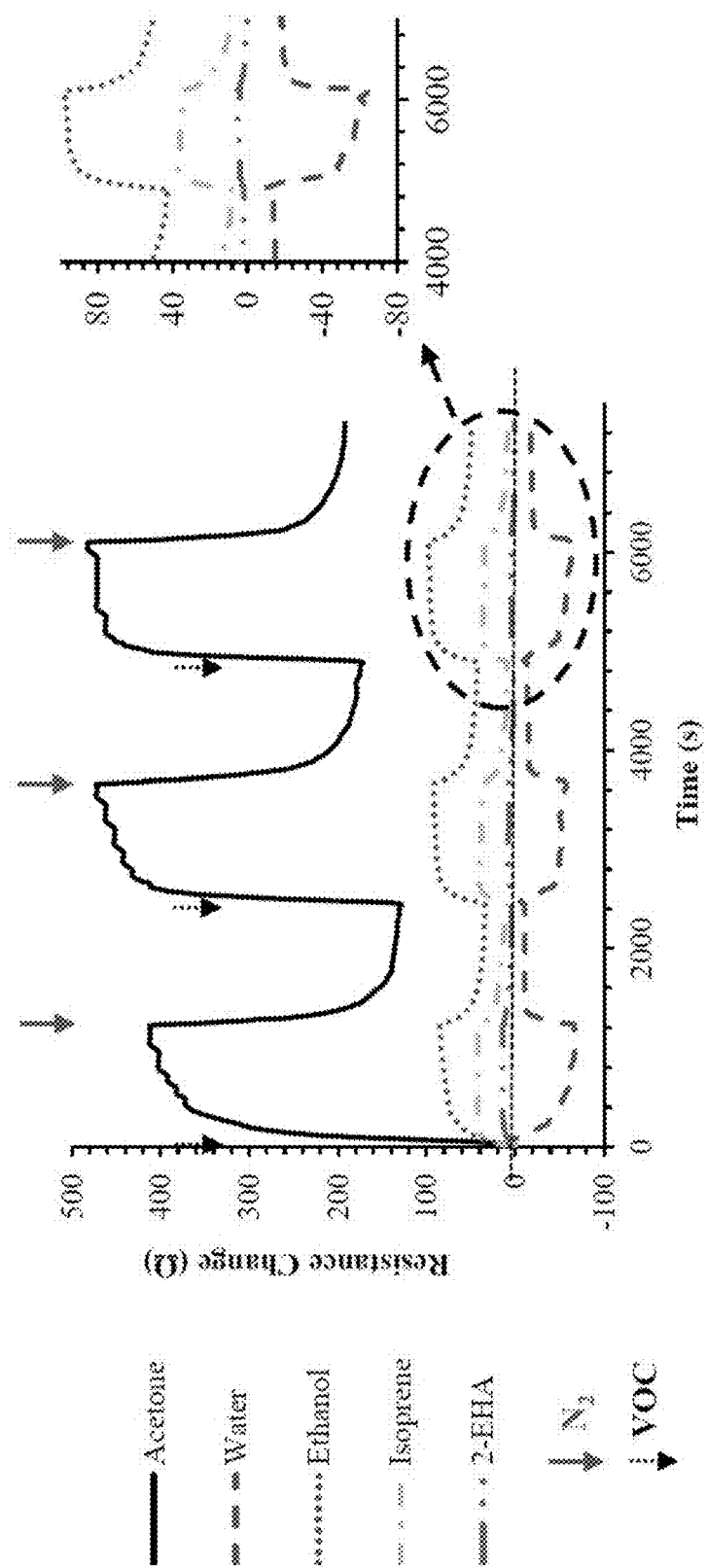
FIG. 25 shows the change in resistance of Sensor-3 of Example 7 in response to exposure to acetone, water, ethanol, isoprene, and 2-EHA.
Figure 26:
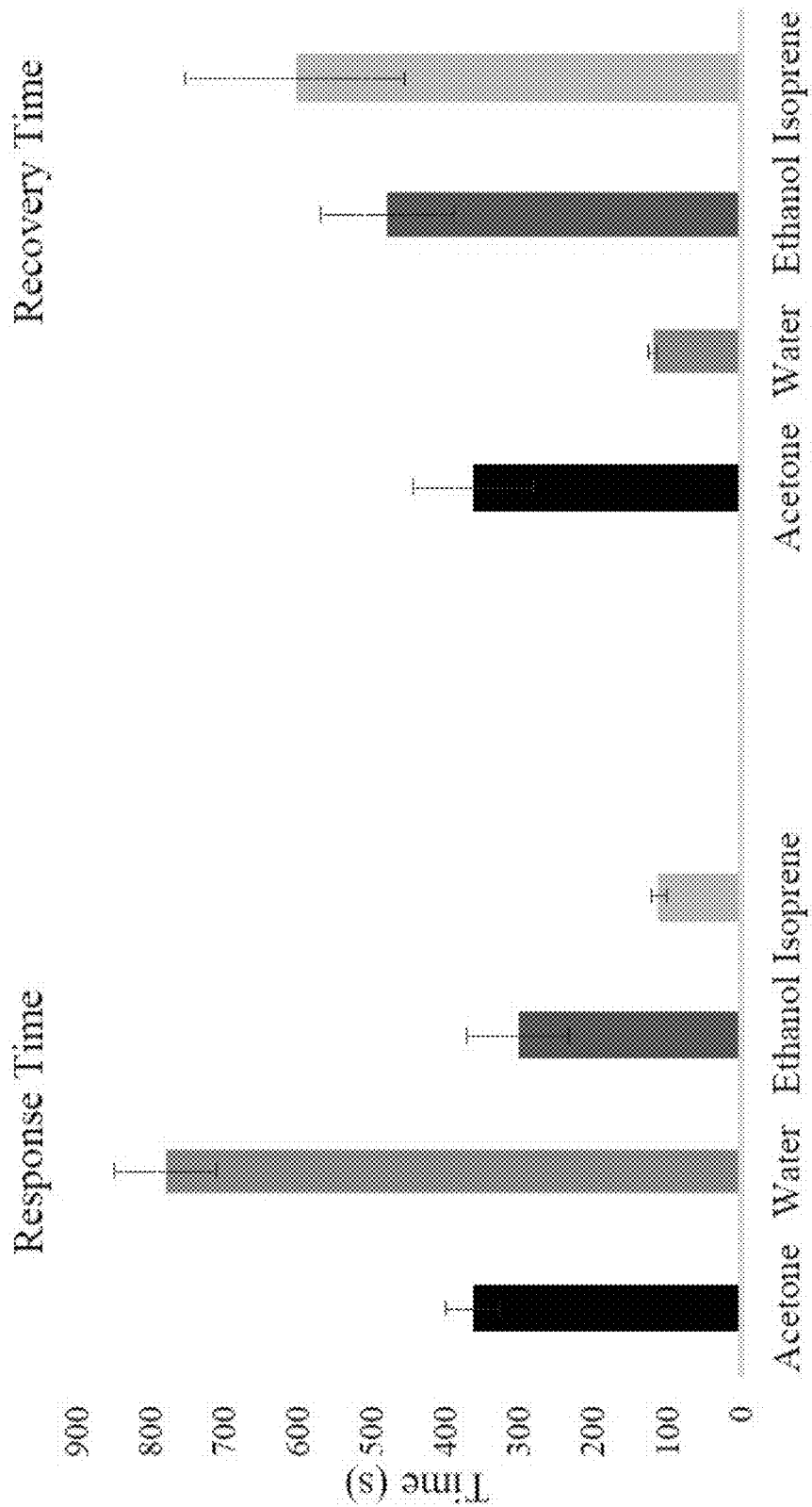
FIG. 26 shows the response and recovery times of Sensor-3 of Example 7 when exposed to acetone, water, ethanol, and isoprene.

Sensor-3 consists of a PVDF-HFP/C65/CNT composite spin coated on a gold IDE. The resistance of the resulting sensor was measured 1.876 kΩ. This sensor was tested with acetone, water, ethanol, isoprene, and 2-EHA using the testing procedure described for Sensor-1 and Sensor-2. The sensor was exposed to a VOC for 20 minutes followed by exposure to nitrogen for next 20 minutes. FIG. 25 shows the measured resistances for the various VOCs. This sensor exhibited a 17.9% increase in resistance when exposed to acetone, while it decreased by 2.4% with water, and increased by 3% with ethanol, 1.5% with isoprene, and 0.3% with 2-EHA. This sensor exhibited high contrast between other VOCs and water, as the resistance decreases with water unlike Sensor-1 and Sensor-2. The response and recovery times are presented in FIG. 26. Response times to acetone and ethanol improved compared to Sensor-1, however the recovery times were higher. This is attributed to the increased affinity of the VOC molecules to the composite material, which reduces the response time and increases the recovery time. For acetone (FIG. 14), it was observed that 20 minutes of exposure was not sufficient to clear out all the adsorbed acetone, thus the resistance did not return to the initial value. However, this duration was sufficient for the other VOCs, perhaps due to the fact that the absorption was much less for these VOCs compared to acetone.

Example 8. Degradation Study

Figure 27:
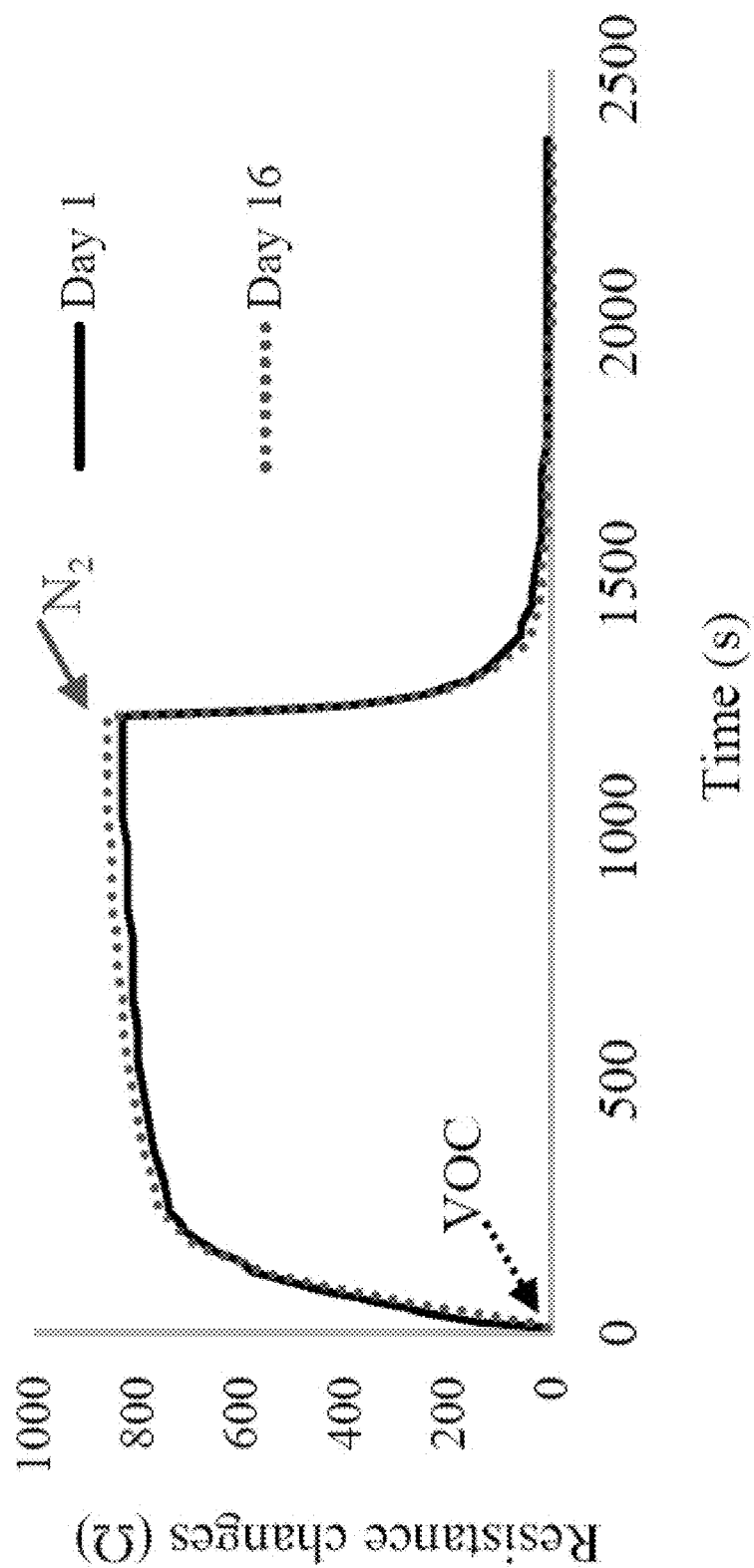
FIG. 27 shows the response of Sensor-2 to acetone on the day of fabrication and after two weeks, as described in Example 8.

To study the degradation of the composite materials of Examples 5 to 7, a sensor of PVDF-HFP/C65/CNT was fabricated and tested with the VOCs over 42 days. During these experiments the sensor was kept in an ambient air environment and exposed to the VOCs and water at various times for over 40 hours of exposure. Over the observed period, the sensor's initial resistance changed by less than 3%. This is attributable to the hydrophobic property of PVDF-HFP which reduces the moisture absorption from the environment. PVDF-HFP is known to offer good stability and resistance against harsh environments. Similarly, a Sensor-2 prepared as described above was tested with acetone on the day of fabrication (Day-1) and after two weeks (Day-16) are shown in FIG. 27. The responses to acetone were similar in both measurements and no significant degradation was observed. Within this period, the sensor was also tested with various VOCs, with over 10 hours of exposure. Additionally, no change in initial resistance was observed from Day-1 to Day-16 (3.04 kΩ).

Example 9. Principle Component Analysis (PCA) for a Sensor System

Figure 28:
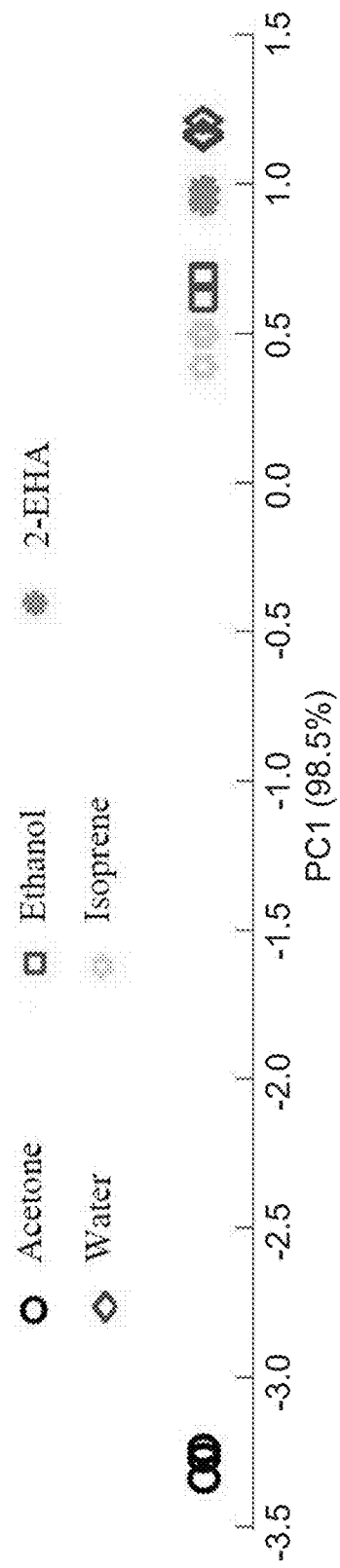
FIG. 28 is a Principle Component Analysis (PCA) plot for extracted features in each of Sensor-1, Sensor-2, and Sensor-3, plotted in percentage of resistance change, as described in Example 9.

The results from the Sensor-1, Sensor-2, and Sensor-3 presented and discussed above were subjected to PCA to demonstrate the selectivity of the combined sensors to the considered VOCs. Table 3 shows resistance changes ($\Delta R = R_{Saturation} - R_{Initial}$) for the three sensors when exposed to the VOCs. The percentage changes in resistances ($\Delta R/R_{Initial}\%$) for the three sensors are also shown in the parentheses in the table. Since the variances of each considered parameter were in the same range, a covariance matrix approach was utilized for the PCA. The change in resistance values shown in Table 3 were used in PCA, which resulted in the three distinctive principal components. From these components the most distinctive component was selected as the feature in the plot shown in FIG. 28. As can be seen in the figure, the VOCs separate from one another. The small variance between the features in the same class shows the repeatability of the sensor response. The variance within each class is much less than the mean between the classes. This assures the selective separation of the VOCs from one another. The distance between the features related to acetone and water is the highest. This indicates the high selectivity of the system to acetone from water. The result shows that extracting one feature from each sensor was sufficient to selectively identify the target VOCs.

TABLE 3

|  | Sensor-1 | Sensor-2 | Sensor-3 |
| --- | --- | --- | --- |
| Water | 3 Ω (0.34%) | 10 Ω (0.32%) | −46 Ω (−2.45%) |
| Acetone | 455 Ω (52.66%) | 800 Ω (26.23%) | 344 Ω (18.33%) |
| Ethanol | 48 Ω (5.56%) | 80 Ω (2.62%) | 28 Ω (1.49%) |
| Isoprene | 26 Ω (3.0%) | 70 Ω (2.3%) | 58 Ω (3.09%) |
| 2-EHA | 1 Ω (0.16% | 10 Ω (0.33%) | 3 Ω (0.16%) |

It should be understood that the methods and apparatuses described above are only exemplary and do not limit the scope of the invention, and that various modifications could be made by those skilled in the art that would fall within the scope of the invention. To apprise the public of the scope of this invention, the following claims are made:

The invention claimed is:

1. A biomedical sensor system for analysis of breath, the sensor system comprising a first sensor, a second sensor, or a third sensor, the first sensor comprising:
- two first sensor electrodes separated by a first sensor gap;
- a first sensor composite material layer located in the first sensor gap and contacting the two first sensor electrodes, the first sensor composite material layer comprising a first poly(vinylidene fluoride-hexafluoropropylene) (PVDF-HFP) composite having a plurality of carbon black particles or gold nanoparticles embedded therein; and
- a first sensor resistance measurement circuit coupled to the two first sensor electrodes to generate an output based on a change in resistance between the two first sensor electrodes;

the second sensor comprising:
- two second sensor electrodes separated by a second sensor gap;
- a second sensor polymeric material layer located in the second sensor gap and covering at least part of the two second sensor electrodes;
- a second sensor composite material layer contacting the second sensor polymeric material layer, the second sensor composite material layer comprising a second PVDF-HFP composite having a plurality of carbon black particles or gold nanoparticles embedded therein; and
- a second sensor resistance measurement circuit coupled to the two second sensor electrodes to generate an output based on a change in resistance between the two second sensor electrodes; and the third sensor comprising:
- two third sensor electrodes separated by a third sensor gap;
- a third sensor composite material layer located in the third sensor gap and contacting the two third sensor electrodes, the third sensor composite material layer comprising a third PVDF-HFP composite having a plurality of carbon black particles and a plurality of carbon nanotubes embedded therein; and
- a third sensor resistance measurement circuit coupled to the third sensor electrodes to generate an output based on a change in resistance between the two third sensor electrodes.

2. The biomedical sensor system of claim 1, the sensor system comprising:
- the first sensor and the second sensor;
- the first sensor and the third sensor; or
- the second sensor and the third sensor.

3. The biomedical sensor system of claim 1, the sensor system comprising the first sensor, the second sensor, and the third sensor.

4. The biomedical sensor system of claim 1, the sensor system comprising more than three sensors.

5. The biomedical sensor system of claim 1, wherein each of the first sensor composite material layer, the second sensor composite material layer, and the third sensor composite material layer has a thickness of about 10 nanometers to about 1 millimeter.

6. The biomedical sensor system of claim 1, wherein the first PVDF-HFP composite having a plurality of carbon black particles or gold nanoparticles embedded therein has a ratio by weight of PVDF-HFP to carbon black particles or gold nanoparticles of 100:1 to 1:10, wherein the second PVDF-HFP composite having a plurality of carbon black particles embedded therein has a ratio by weight of PVDF-HFP to carbon black particles of 100:1 to 1:10, and wherein the third PVDF-HFP composite having a plurality of carbon black particles and a plurality of carbon nanotubes embedded therein has a ratio by weight of PVDF-HFP to carbon black of 100:1 to 1:10 and a ratio by weight of PVDF-HFP to carbon nanotubes of 100:1 to 1:5.

7. The biomedical sensor system of claim 1, the sensor system comprising the first sensor or the second sensor, the first and second PVDF-HFP composites each having a plurality of gold nanoparticles embedded therein, and the plurality of gold nanoparticles having a surface coating of one or more functional groups selected from the group consisting of $C_1$-$C_9$ thiol-alkanes, $C_{10}$-$C_{20}$ thiol-alkanes, $C_2$-$C_9$ thiol-aromatics, $C_{10}$-$C_{20}$ thiol-aromatics, and combinations thereof.

* * * * *